United States Patent

Barbier et al.

Patent Number: 5,914,406
Date of Patent: Jun. 22, 1999

[54] AZEPANES AND THEIR RING HOMOLOGUES HAVING PROTEIN KINASE INHIBITING ACTIVITY

[75] Inventors: Pierre Barbier, Rixheim, France; Isabelle Huber, Geneva, Switzerland; Fernand Schneider; Josef Stadlwieser, both of Basle, Switzerland; Sven Taylor, Riedisheim, France

[73] Assignee: Hoffman-LA Roche Inc., Nutley, N.J.

[21] Appl. No.: 09/019,876

[22] Filed: Feb. 6, 1998

Related U.S. Application Data

[62] Division of application No. 08/706,896, Sep. 3, 1996, Pat. No. 5,750,706, which is a division of application No. 08/368,690, Jan. 4, 1995, Pat. No. 5,583,222.

[30] Foreign Application Priority Data

Jan. 12, 1994 [CH] Switzerland ............................ 088/94

[51] Int. Cl.$^6$ .................................................. C07D 401/12
[52] U.S. Cl. ........................... 546/213; 546/194; 546/207; 546/208; 544/360; 544/359
[58] Field of Search ..................... 546/208, 207, 546/213, 194; 544/359, 360

[56] References Cited

U.S. PATENT DOCUMENTS 5,583,222  12/1996  Barbier et al. .......................... 540/596
5,750,706   5/1998  Barbier et al. ....................... 546/279.1

Primary Examiner—Mukund J. Shah
Assistant Examiner—Pavanaram K. Sripada
Attorney, Agent, or Firm—George W. Johnston; Dennis P. Tramaloni

[57] ABSTRACT

The compounds of formula I:

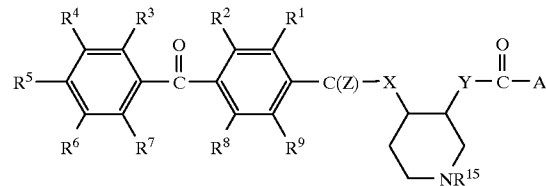

wherein $R^1$—$R^9$, $R^{15}$, A, X, Y, and Z have the meaning given in the specification are active as protein kinase inhibitors and can be used as medicaments, particularly for the treatment of inflammatory skin disorders and alopecia.

3 Claims, No Drawings

AZEPANES AND THEIR RING HOMOLOGUES HAVING PROTEIN KINASE INHIBITING ACTIVITY

This is a divisional of application Ser. No. 08/706,896 filed Sep. 3, 1996 now U.S. Pat. No. 5,750,706, which is a Division Ser. No. 08/368,690, filed Jan. 4, 1995 (now U.S. Pat. No. 5,583,222).

SUMMARY OF THE INVENTION

The present invention is concerned with novel azepanes and their ring homologues of the formula:

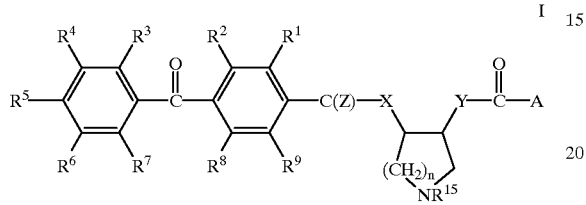

wherein
A is a residue

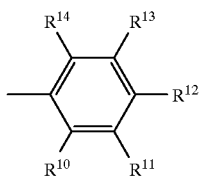

2-, 3- or 4-pyridyl or 2- or 3-piperazinyl, or 2-, 3- or 4-pyridyl or 2- or 3-piperazinyl substituted by one or more lower-alkyl, lower-alkoxy and hydroxy groups;

X and Y each independently are oxygen or NH, but are not both NH;

Z is oxygen or, where X is oxygen, oxygen or H,H; n is 1, 2 or 3;

$R^1$ is hydrogen;

$R^2$ is hydrogen or fluorine;

$R^3$ is hydrogen, hydroxy, lower-alkoxy, fluorine, trifluoromethyl, lower-alkoxycarbonyl, tetrazolyl or tetrazolyl substituted by lower-alkyl, benzyl, cyanomethyl or carbamoyl-methyl;

$R^4$ is hydrogen, hydroxy, lower-alkoxy, lower-alkyl, chlorine, fluorine, trifluoromethyl, acetyl, di-lower-akylamino, or lower-alkoxy-lower-alkyl, lower-alkylthio, lower-alkylsulphonyl, phenyl, pyrrolidinyl or piperidinyl;

$R^5$ is hydrogen, lower-alkoxy, fluorine or trifluoromethyl;

$R^6$ is hydrogen, hydroxy, lower-alkoxy, fluorine, 2,4-difluorophenyl, lower-alkoxy-lower-alkyl, lower-alkanoyl, benzoyl, nitrilo, trifluoromethyl, cyclo-lower-alkyl, 2-or 4-thiazolyl, 2-thiazolidinyl, 2-oxazolyl or 2-oxazolidinyl, 2-or 4-imidazolyl;

$R^7$ is hydrogen, hydroxy, lower-alkoxy, amino or fluorine;

$R^6$ and $R^7$ together are a residue —N=CH—CH=N— or —N(CH$_3$)CH$_2$CH$_2$N(CH$_3$)—;

$R^8$ is hydrogen or fluorine;

$R^9$ is hydrogen;

$R^{10}$ is hydrogen, hydroxy, lower-alkoxy or lower-alkyl;

$R^{11}$ is hydrogen, lower-alkoxy, lower-alkyl, fluorine or bromine;

$R^{12}$ is hydrogen, hydroxy, lower-alkoxy, carboxy, lower-alkoxycarbonyl or amino;

$R^{13}$ is hydrogen, hydroxy, lower-alkoxy, lower-alkyl, acetyl or fluorine;

$R^{14}$ is hydrogen, lower-alkyl or fluorine;

$R^{15}$ is hydrogen or amidino;

$R^3$ and $R^4$ together are a residue —CH=CH—CH=CH— or ethylenedioxy;

$R^4$ and $R^5$ together are a residue —CH=CH—CH=CH—, tetra-methylene, methylenedioxy, ethylenedioxy or a residue —N=CH—CH=CH— or a residue (a)

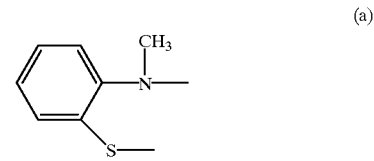

in which the sulfur atom is bonded at the $R^5$ position; and $R^{12}$ and $R^{13}$ together are a residue —CH=CH—CH=CH— or —C(OH)=CH—CH=CH— in which the carbon atom carrying the hydroxy group is bonded at the $R^{12}$ position;

and pharmaceutically acceptable salts thereof.

The invention is also concerned for the preparation of the compounds of formula I, pharmaceutical compositions containing a compound of formula I or a pharmaceutically acceptable salt thereof in the manufacture of pharmaceutical compositions for the therapy and prophylaxis of conditions which are mediated by protein kinases.

DETAILED DESCRIPTION OF THE INVENTION

The term "lower" used here denotes groups with 1–6, preferably 1–4, C atoms. Alkyl and alkoxy groups can be straight-chain or branched, such as methyl, ethyl, propyl, isopropyl, n-butyl, sec.- and tert.-butyl, pentyl and hexyl and, respectively, methoxy, ethoxy, propoxy, isopropoxy, n-butoxy, sec. and tert.- butoxy, pentyloxy and hexyloxy. Alkanoyl denotes acid residues of aliphatic, saturated and unsaturated carboxylic acids, the hydrocarbon residues of which can be straight-chain or branched.

One embodiment of the invention are compounds of the formula:

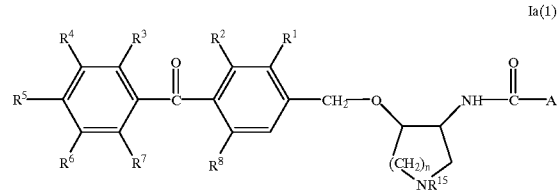

wherein the R-groups, A and n are as in formula I. Preferred compounds of formula Ia(1) are those wherein n is 3, $R^3$ is hydroxyl, $R^6$ is methoxy, $R^2$, $R^4$, $R^5$, $R^7$, $R^8$ and $R^{15}$ are hydrogen, and A is $A^1$.

A preferred embodiment of the invention are compounds of the formula:

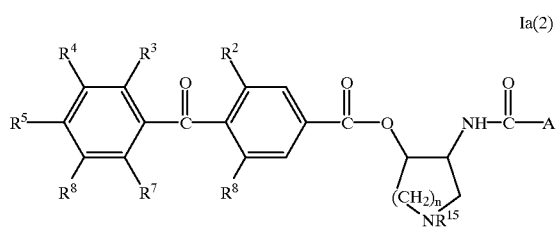

Ia(2)

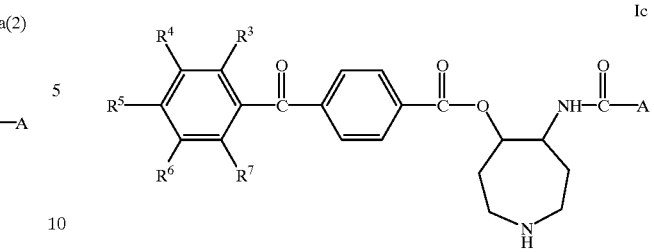

Ic wherein the R-groups, A and n are as in formula I. Preferred compounds of formula Ia(2) are those wherein $R^2$ and $R^8$ are flourine. Especially preferred are those wherein $R^2$ and $R^8$ are flourine, n is 3, $R^{15}$ is hydrogen, and A is $A^1$.

A further embodiment of the invention comprises compounds of the formula:

wherein the R-groups and A are as in formula I.
Particularly preferred are compounds of the formula:

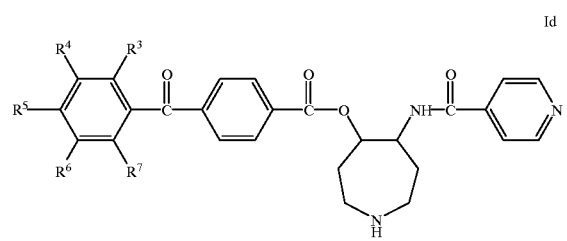

Id

Especially preferred are compounds of the formula:

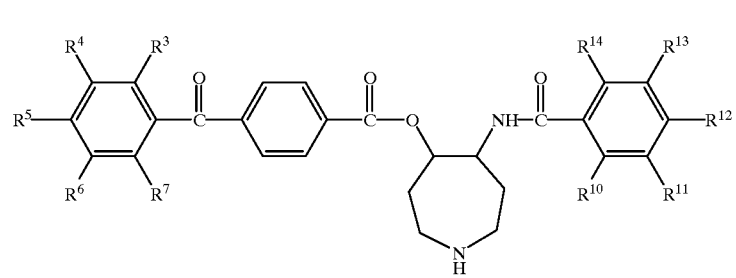

Ie

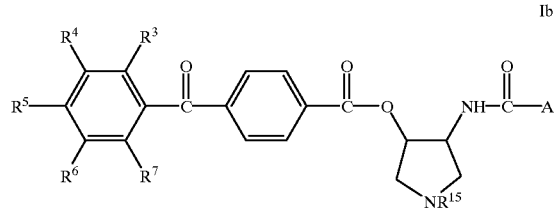

Ib wherein the R-groups and A are as in formula I. $R^{15}$ is preferably hydrogen, A is preferably $A^1$ or 4-pyridyl. When A is $A^1$, $R^{10}$ and $R^{14}$ are preferably hydrogen, $R^{11}$ and $R^{13}$ are preferably both hydrogen or methyl, and $R^{12}$ is preferably hydroxyl.

A preferred embodiment of the invention comprises compounds of the formula:

In general, the preferred compounds of formula Ie are compounds wherein $R^3$ is hydrogen, fluorine or hydroxyl; $R^5$ is hydrogen; $R^6$ is hydrogen or lower alkoxy, especially hydrogen; $R^7$ is hydrogen, hydroxyl, or flourine, especially hydroxyl; $R^{10}$ is hydrogen, hydroxyl or lower alkyl, especially hydrogen; $R^{12}$ is hydrogen, lower-alkoxy, or hydroxyl, especially hydroxyl; $R^{13}$ is hydrogen, lower-alkoxy, or lower-alkyl; and $R^{14}$ is hydrogen.

In particular, preferred are compounds of formula Ie wherein $R^{10}$ is hydrogen, hydroxyl or lower alkyl; $R^{12}$ is hydrogen, lower-alkoxy, or hydroxyl; $R^{13}$ is hydrogen, fluorine, lower-alkoxy, or lower-alkyl; and $R^{14}$ is hydrogen or methyl; particularly wherein $R^{10}$, $R^{11}$, $R^{13}$ and $R^{14}$ are hydrogen and $R^{12}$ is hydroxyl, or wherein $R^{10}$ and $R^{14}$ are hydrogen, $R^{11}$ and $R^{13}$ are methyl, and $R^{12}$ is hydroxyl, or wherein $R^{10}$ and $R^{14}$ are hydrogen, $R^{11}$ and $R^{13}$ are methoxy, and $R^{12}$ is hydroxyl.

Also preferred are compounds of formula Ie wherein $R^3$ is hydrogen, fluorine or hydroxyl; $R^5$ is hydrogen, fluorine or methoxy, especially hydrogen; $R^6$ is hydrogen or lower alkoxy, especially methoxy; $R^7$ is hydrogen, hydroxyl, or flourine; particularly wherein additionally $R^{11}$ and $R^{14}$ are hydrogen or lower-alkoxy and $R^{12}$ is hydrogen; and more particularly wherein $R^4$ is hydrogen or methoxy.

Also preferred are compounds of formula Ie wherein $R^3$ is hydrogen, fluorine or hydroxyl; $R^5$ is hydrogen, fluorine or methoxy; $R^6$ is hydrogen or lower alkoxy; $R^7$ is hydrogen, hydroxyl, or flourine; and $R^{11}$, $R^{12}$, and $R^{13}$ are all methoxy.

Also preferred are compounds of formula Ie wherein $R^3$ is hydrogen, fluorine or hydroxyl; $R^5$ is hydrogen, fluorine or methoxy; $R^6$ is hydrogen or lower alkoxy; $R^7$ is hydrogen, hydroxyl, or flourine, especially hydroxyl; and $R^{12}$ is hydroxyl; particularly wherein additionally $R^{10}$ is hydrogen or methyl, $R^{11}$ is hydrogen, lower-alkyl or lower-alkoxy, and $R^{13}$ is hydrogen, lower-alkyl or methoxy.

The substituents on the heterocylic ring in compounds of the invention can have the trans or cis configuration. The trans configuration is preferred.

The compounds of the invention and their pharmaceutically usable salts are protein kinase inhibitors; they inhibit protein kinase-mediated cellular processes such as cell proliferation and cell secretion, and can therefore be used for the treatment or prevention of illnesses which are mediated by protein kinases. Examples of diseases which are known to be mediated by protein kinases are inflammatory diseases such as arthritis, immune diseases, psoriasis, contact dermatitis, organ transplant rejection, as well as some cancers. Due to their pharmacological activity as protein kinase inhibitors, the compounds of the invention inhibit HIV (human immunodeficiency virus) or Epstein-Barr virus from infecting cells, and are therefore suitable for the treatment of AIDS and infectious mononucleosis.

Furthermore, the compounds of the invention inhibit smooth muscle contraction and can therefore be used for the treatment of cardiovascular and bronchopulmonary illnesses in which the inhibition of smooth muscle contraction would be beneficial to the patient. Further, the activity of the compounds of the invention as inhibitors of smooth muscle contraction make them useful for the treatment of asthma.

The compounds of the invention also inhibit blood platelet aggregation. Such an activity would make the compounds useful for the treatment or prevention of thromboses. Furthermore, the compounds of the invention inhibit the liberation of mediators of activated neutrophils which are known to be a source of ischemic damage to the heart and brain. The compounds of the invention can therefore be used in the control of ischemic damage, e.g., in the heart or brain. Further, they inhibit neurotoxicity caused by increased glucose level and are therefore of value in the treatment of diabetic complications. Finally, the compounds in accordance with the invention stimulate hair growth and can therefore be used for the prevention or suppression of hair loss.

Protein kinases play an important role as signal transmitters in many cell functions. In addition to tyrosine kinases, serine/threonine kinases such as protein kinase C (PKC) and cyclic AMP-dependent protein kinase (PKA) are key enzymes in the signal transmission chain from the cell membrane to the cell nucleus.

The compounds in accordance with the invention inhibit serine/protein kinases such as PKC and PKA not only as the isolated enzyme but also in cells. They therefore inhibit important cell functions as mentioned above, especially the activation and proliferation of T-lymphocytes and the proliferation of keratinocytes.

Inhibitors of T-cell activation can be used as immunosuppressives for use in illnesses such as rheumatoid arthritis, psoriasis and other inflammatory skin disorders (atopic eczema, contact eczema), in autoimmune diseases, transplants and immunomediated alopecia.

Inhibitors of keratinocyte proliferation are of value for use in skin diseases having a hyperproliferative component in the epidermis, especially psoriasis. Inhibitors of cell proliferation can also be used in oncology.

The aforementioned activities of the compounds of the invention may be determined by any conventional means, but preferably are measured using the test procedures described hereinafter:

A: Inhibition of protein kinase C (PKC) (isolated enzyme)

Protein kinase C (PKC) activity is determined by measuring the transfer of $^{32}$P-labelled phosphate from $^{32}$P-γ-ATP (10 μM) to histone H1 (200 μg/ml) as the substrate. Partially purified PKC from swine brain is used as the enzyme source [DEAE chromatography according to the method of U. Kikkawa et al. (Methods Enzymol. 99, 288, 1983)]. Activation of the PKC is effected by phospholipid vesicle prepared by ultrasound treatment of a mixture of 0.05 ml of phosphatidylserine (10 mg/ml) and 0.005 ml of diolein (10 mg/ml) in 5 ml of Tris-HCl buffer (20 mM, pH 7.4). The test substances are used in dimethyl sulphoxide (DMSO)/buffer in the concentration range 0.001–100 μM. The test is started by the addition of enzyme; after incubation at 32° C. for 2 minutes the reaction is stopped by the addition of 20% trichloroacetic acid (with 1% SDS and 1% sodium pyrophosphate). The precipitated radioactive histone protein is separated from excess ATP by filtration over nitrocellulose membranes and the radioactivity on the filter is measured in a scintillation counter. The inhibitory activity of the test substance is given as the micromolar concentration which is required to reduce the PKC activity by 50% ($IC_{50}$ [μM]).

B: Inhibition of cAMP-dependent protein kinase (PKA)

PKA activity is determined by measuring the transfer of $^{32}$P-labelled phosphate from $^{32}$P-γ-ATP (10 μM) to histone H1 (333 μg/ml) as the substrate. Partially purified PKA from swine brain is used as the enzyme source [DEAE chromatography according to the method of U. Kikkawa et al. (Methods Enzymol. 99, 288, 1983)]. Activation of the PKA is effected by cyclic AMP (2 μM) in Tris-HCl buffer (20 mM, pH 7.4). The test substances are used in dimethyl sulphoxide (DMSO)/buffer in the concentration range 0.001–100 μM. The test is started by the addition of enzyme; after incubation at 32° C. for 2 minutes the reaction is stopped by the addition of 20% trichloroacetic acid (with 1% SDS and 1% sodium pyrophosphate). The precipitated radioactive histone protein is separated from excess ATP by filtration over nitrocellulose membranes and the radioactivity on the filter is measured in a scintillation counter. The inhibitory activity of the test substance is given as the micromolar concentration which is required to reduce the PKA activity by 50% ($IC_{50}$ [μM]).

C: Inhibition of protein kinase C (PKC) (in cells)

The intracellular protein kinase C (PKC) activity is determined in 3T3 fibroblasts by measuring the phosphorylation of a PKC-specific substrate, namely 80 kD MARCKS protein (myristoylated alanine-rich C-kinase substrate). The endogenous ATP is firstly labelled by incubating the cells at 37° C. with 80–200 μCi/ml of inorganic $^{32}$P-labelled phosphate. Then, the activation of the PKC is effected by phorbol ester (tetradecanoyl-phorbol 13-acetate (TPA); 100 nM). The test substances are used 15 minutes prior to TPA in dimethyl sulphoxide (DMSO)/buffer in the concentration range 0.1–100 μM. After incubation at 37° C. for 15 minutes the reaction is stopped by removing the medium and the cells are lysed by the addition of 1% Triton X-100 in phosphate buffer. The cell extract is subjected to a heat treatment (20 minutes at 90° C.) and subsequently centrifuged, whereby the MARCKS protein remains dissolved in the supernatant. This is then separated by discontinuous, one-dimensional SDS gel electrophoresis and the radioactivity in the 80 kD protein band is measured by a phosphoimager. The inhibitory activity of the test substance is given as the micromolar concentration which is required to reduce the PKC activity by 50% ($IC_{50}$ [μM]) in comparison to control samples without inhibitor.

Inhibition of T-lymphocyte proliferation

Human mononuclear cells are isolated from venous blood of a healthy donor and a suspension of $5 \times 10^5$ cells/ml in RPMI 1640 medium, which contains 10% FCS, is prepared. The cells are stimulated with 1 µg/ml of T-cell-specific mitogen phytohaemagglutinin (PHA). 200 µl aliquots of cell suspension are treated in microtitre plates with the test substances in serial dilutions in the concentration range 0.03–10 µM. The cell proliferation is measured on the 3rd and 4th day by incubation with 1 µCi of [$^3$H] thymidine during the last 6 hours of the respective day. The radioactivity taken up is measured with a liquid scintillation counter.

E Inhibition of keratinocyte proliferation a) HaCaT-cells (immortalised human cells line):

HaCaT-cell culture is effected in medium DMEM/F12 (mixture ratio 3/1) which contains serum (FCS, 5%), epidermal growth factor (EGF), hydrocortisone, cholera toxin, insulin, L-glutamine and penicillin/streptomycin. 5000 cells in 0.2 ml of medium are used per well in microtitre plates. The test substances are diluted in dimethyl sulphoxide/ (DMSO)/medium and used in the concentration range 0.01–10 µM at the start of the culture. The cells are then incubated at 37° C. for 48 hours; radioactive [$^3$H]thymidine is added during the last 6 hours. After disrupting the cells with trypsin incorporated activity is measured in a scintillation counter. The inhibitory activity of the test substance is given as the micromolar concentration which is required to reduce the thymidine incorporation by 50% (IC$_{50}$[µM]).

b) Primary keratinocytes

Keratinocytes, isolated from human foreskin, are used in the primary culture up to passage 7. The culture and test conditions are identical with those of the HaCaT-cells with the exception of the use of 10000 cells per well.

The results obtained with typical compounds of formula I in these test procedures are compiled in the following Table:

| Compound of Example | Test Procedure * | | | | |
|---|---|---|---|---|---|
| | A | B | C | D | E |
| 20 | 0.011 | 0.015 | 0.34 | 0.1–6 | a: 3–10 |
| 25 | 0.040 | 0.014 | 0.8 | 1 | |
| 41 | 0.040 | 0.013 | >1 | 0.3 | |
| 57 | 0.867 | 0.005 | 2.0 | | a: 0.3–0.6 |
| | | | | | b: 0.6 |
| 60 | 1.2 | 0.009 | 2.7 | 2–5 | a: 0.3–0.5 |
| | | | | | b: 0.3–6 |

* the test data indicate the respective IC$_{50}$ [µM]

The compounds of formula I and their salts can be used as medicaments, e.g., in the form of pharmaceutical preparations.

The preparations can be administered enterally, parenterally or topically. Preparations in the form of tablets, capsules, dragees, syrups, suspensions, solutions and suppositories are suitable, e.g., for enteral administration. Preparations in the form of infusion or injection solutions are suitable for parenteral administration.

The dosages in which the preparations are administered can vary according to the mode of use and route of use and on the requirements of the patient.

In the case of the oral administration of the compounds of the invention, dosages of about 0.1–100 mg/kg, preferably 0.5–50 mg/kg, per day come into consideration for adults.

The preparations can be administered in one or several dosages. Capsules containing about 5–500 mg of active ingredient represent a preferred dosage form.

The preparations can contain inert as well as pharmacodynamically active additives. Tablets or granulates, e.g., can contain a series of binders, fillers, carrier substances or diluents. Liquid preparations are also contemplated, for example, in the form of a sterile, water-miscible solution. Capsules can contain, in addition to the active ingredient, a filler or thickener. Furthermore, flavour-improving additives as well as substances usually used as preservatives, stabilizers, water-retainers and emulsifiers as well as salts for varying the osmotic pressure, buffers and other additives can also be present.

The previously mentioned carrier substances and diluents can be organic or inorganic substances, e.g., water, gelatine, lactose, starch, magnesium stearate, talc, gum arabic, polyalkylene glycols and the like. It is a prerequisite that all adjuvants used in the manufacture of the preparations are non-toxic.

For topical use the active ingredients are conveniently used in the form of ointments, tinctures, creams, solutions, lotions, sprays, suspensions and the like. Ointments and creams as well as solutions are preferred. These preparations destined for topical use can be manufactured by admixing the process products as active ingredients with non-toxic, inert, solid or liquid carriers which are suitable for topical treatment and which are conventional in such preparations.

For topical use there are suitable conveniently about 0.1–5%, preferably 0.3–3%, solutions as well as about 0.1–5%, preferably about 0.3–2%, ointments and creams.

If desired, an antioxidant, e.g. tocopherol, N-methyl-γ-tocopheramine as well as t-butyl-hydroxyanisole or t-butyl-hydroxytoluene, can be admixed with the preparations.

The compounds of the invention and their salts can be prepared in accordance with the invention by cleaving off the protecting group R$^{16}$ and, if necessary, hydroxy and amino protecting groups present as R$^3$, R$^4$, R$^6$, R$^7$, R$^{12}$ and R$^{13}$ from a compound of the formula:

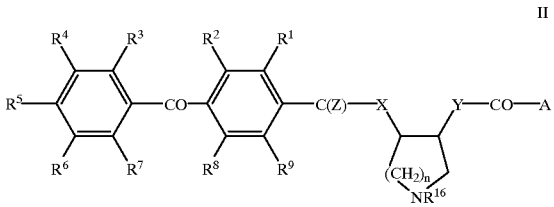

wherein R$^{16}$ is a protecting group and the remaining symbols are as in formula I, above, whereby hydroxy and amino groups represented by R$^3$, R$^4$, R$^6$, R$^7$, R$^{12}$ and R$^{13}$ can be present in protected form, and if desired, converting the compound obtained in which R$^{15}$ represents hydrogen into a compound in which R$^{15}$ represents amidino and, if desired, converting the resulting compound of the invention into a pharmaceutically acceptable salt.

Examples of protecting groups R$^{16}$ and of amino protecting groups present in the substituents R$^7$ and R$^{12}$ are groups which are known for the protection of amino groups, such as tert.-butoxycarbonyl. Methoxymethyl and silyl groups such as tert.-butyl-dimethyl-silanyl are examples of hydroxy protecting groups.

The cleavage of these protecting groups can be carried out in a manner known per se by treatment with acids, e.g. mineral acids such as HCl, in an inert organic solvent, e.g., an ether such as dimethoxyethane or an alcohol such as isopropanol or mixtures of such solvents. The cleavage of the protecting groups is conveniently effected at low temperatures, preferably at temperatures below room temperature, especially at about 0° C.

The introduction of an amidino group into a compound of the invention in which $R^{15}$ is hydrogen can be effected in a manner known per se, e.g., by reaction with formamidine derivatives such as formamidinesulphonic acid.

The compounds of the invention form salts into which they can be converted in a manner known per se. Examples of pharmaceutically acceptable salts of the compounds of the invention are acid addition salts of mineral acids, particularly hydrochlorides.

Compounds of formula II in which Z and X represent oxygen can be obtained from compounds of the formula:

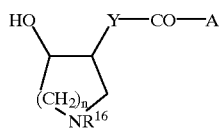

III in which Y, A, $R^{16}$ and n have the significance given above, by reaction with an acid of the formula:

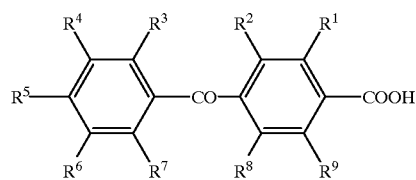

IV in which $R^1$–$R^9$ have the significance given above, or a reactive derivative thereof.

Compounds of formula II in which X signifies NH can be obtained from compounds of the formula:

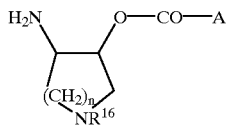

V in which A, $R^{16}$ and n have the significance given above, by reaction with a compound of formula III or a reactive derivative thereof.

Compounds of formula II in which Z signifies H,H and Y signifies NH can be obtained from compounds of the formula:

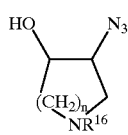

VI in which $R^{16}$ and n have the significance given above, by reaction which a compound of the formula:

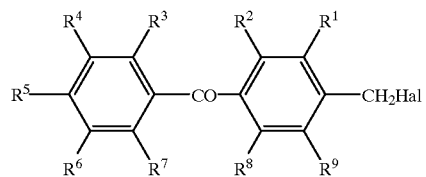

VII in which Hal signifies halogen, especially bromine, and $R^1$–$R^9$ have the significance given above,
and subsequent reaction of the resulting ether with an acid of the formula A—COOH.

Examples for the preparation of the compounds of formula II are given in detail hereinafter. Other substituted compounds of formula II can be prepared by analogy to these Examples.

EXAMPLES

Example A

A. The starting materials used in Examples 1–64 were prepared as follows by esterifying an alcohol (see Example B) with an acid activated by sulphonyl chloride or carbodiimide (see Example C):

A 1 207 mg of 1-(3-dimethylaminopropyl)-3-ethylcarbodiimide hydrochloride were added to a mixture of 445 mg of tert-butyl (3R,4R)-3-[4-[dimethyl-(1,1,2-trimethylpropyl)-silanyloxy]-benzoylamino]-4-hydroxy-azepane-1-carboxylate 350 mg of 3,5-difluoro-4-(5-methoxy-2-methoxymethoxy-benzoyl)benzoic acid (Example C 26) and 33 mg of N,N-dimethylaminopyridine in dichloromethane. The mixture was stirred at room temperature overnight, poured into a pH 7 buffer solution and the organic components were extracted with ethyl acetate. The combined extracts were washed with sodium chloride solution, dried and evaporated. The oily residue was purified by column chromatography on silica gel (eluent: hexane/ethyl acetate 2:1) and yielded 760 mg of tert-butyl (3R,4R)-4-[(3,5-difluoro-4-(5-methoxy-2-methoxymethoxy-benzoyl) benzoyloxy]-3-[4-[dimethyl-(1,1,2-trimethylpropyl)-silanyloxy]-benzoylamino]-4-hydroxy-azepane-1-carboxylate as a colourless foam which was used further in this form.

In analogy there were prepared:

A 2 tert-Butyl (3R,4R)-4-[4-(2-fluoro-4-methoxy-6-methoxy-methoxy-benzoyl)-benzoyloxy]-3-(4-methoxymethoxy-benzoyl-amino)-azepane-1-carboxylate as a colourless foam from tert-butyl (3R,4R)-4-hydroxy-3-(4-methoxymethoxy-benzoylamino)-azepane-1-carboxylate (Example B 2) and 4-(2-fluoro-4-methoxy-6-methoxymethoxy-benzoyl)-benzoic acid (Example C 1)
MS: m/e=711.7 (M+H)$^+$
IR (KBr): 1719, 1668, 1623, 1579, 1501 cm$^{-1}$ A 3 tert-Butyl (3R,4R)-4-[4-(2-fluoro-6-methoxymethoxy-benzoyl)-benzoyloxy]-3-(3-methoxy-4-methoxymethoxy-benzoyl-amino)-azepane-1-carboxylate as a colourless foam from tert-butyl (3R,4R)-4-hydroxy-3-(3-methoxy-4-methoxymethoxy-benzoylamino)-azepane-1-carboxylate (B3) and 4-(2-fluoro-6-methoxymethoxy-benzoyl)-benzoic acid (C2)
MS: m/e=711.4 (M+H)$^+$
IR (KBr): 1720, 1683, 1613, 1583, 1503 cm$^{-1}$ A 4 tert-Butyl (3R,4R)-4-[4-(2-fluoro-6-methoxymethoxy-benzoyl)-benzoyloxy]-3-(5-methoxy-2-methoxymethoxy-benzoylamino)-azepane-1-carboxylate as a colourless foam from tert-butyl (3R,4R)-4-hydroxy-3-(5-methoxy-2-methoxymethoxy-benzoylamino)-azepane-1-carboxylate (B4) and 4-(2-fluoro-3-methoxy-6-methoxymethoxy-benzoyl)-benzoic acid (C3)

A 5 tert-Butyl (3R,4R)-3-[4-(tert-butyldimethylsilanyloxy)-benzoylamino]-4-(3-methoxymethoxy-naphthalen-2-ylcarbonyl)-benzoyl]-azepane-1-carboxylate as a colourless foam from tert-butyl (3R,4R)-3-[4-(tert-butyldimethylsilanyloxy)-benzoylamino]-4-hydroxy-azepane-1-carboxylate (B5) and 4-(3-methoxymethoxy-naphthalen-2-ylcarbonyl)-benzoic acid (C4)

A 6 tert-Butyl (3R,4R)-4-[4-(2-fluoro-4-methoxy-6-methoxy-methoxy-benzoyl)-benzoyloxy]-3-(3,5-dimethoxy-4-methoxy-methoxy-benzoylamino)-azepane-1-carboxylate as a colourless foam from tert-butyl (3R,4R)-4-hydroxy-3-(3,5-dimethoxy-4-methoxymethoxy-benzoylamino)-azepane-1-carboxylate (B6) and 4-(2-fluoro-4-methoxy-6-methoxymethoxy-benzoyl)-benzoic acid (C1)
MS: m/e -771.5 (M+H)+
IR (KBr): 1720, 1672, 1621, 1582, 1495 cm−1

A 7 tert-Butyl (3R,4R)-4-[4-(2-fluoro-6-methoxymethoxy-benzoyl)-benzoyloxy]-3-(3,5-dimethoxy-4-methoxymethoxy-benzoylamino)-azepane-1-carboxylate as a colourless foam from tert-butyl (3R,4R)-4-hydroxy-3-(3,5-dimethoxy-4-methoxy-methoxy-benzoylamino)-azepane-1-carboxylate (B6) and 4-(2-fluoro-6-methoxymethoxy-benzoyl)-benzoic acid (C2)
MS: m/e=741.5 (M+H)+
IR (KBr): 1720, 1680, 1610, 1586, 1493 cm−1

A 8 tert-Butyl (3R,4R)-4-[4-(2,3-difluoro-6-methoxymethoxy-benzoyl)-benzoyloxy]-3-(3,5-dimethoxy-4-methoxymethoxy-benzoylamino)-azepane-1-carboxylate as a colourless foam from tert-butyl (3R,4R)-4-hydroxy-3-(3,5-dimethoxy-4-methoxy-methoxy-benzoylamino)-azepane-1-carboxylate (B6) and 4-(2,3-difluoro-6-methoxymethoxy-benzoyl)-benzoic acid (C5)
MS: m/e=759.5 (M+H)+
IR (KBr): 1721, 1684, 1587, 1494 cm−1

A 9 tert-Butyl (3R,4R)-4-[4-(2,4-difluoro-6-methoxymethoxy-benzoyl)-benzoyloxy]-3-(3,5-dimethoxy-4-methoxymethoxy-benzoylamino)-azepane-1-carboxylate as a colourless foam from tert-butyl (3R,4R)-4-hydroxy-3-(3,5-dimethoxy-4-methoxy-methoxy-benzoylamino)-azepane-1-carboxylate (B6) and 4-(2,4-difluoro-6-methoxymethoxy-benzoyl)-benzoic acid (C6)
MS: m/e=759.5 (M+H)+
IR (KBr): 1720, 1673, 1606, 1493 cm−1

A 10 tert-Butyl (3R,4R)-4-[4-(2-fluoro-3-methoxy-6-methoxy-methoxy-benzoyl)-benzoyloxy]-3-(4-methoxymethoxy-benzoyl-amino)-azepane-1-carboxylate as a colourless foam from tert-butyl (3R,4R)-4-hydroxy-3-(4-methoxymethoxy-benzoylamino)-azepane-1-carboxylate (B6) and (2-fluoro-3-methoxy-6-methoxymethoxy-benzoyl)-benzoic acid (C3)
MS: m/e=711.6 (M+H)+
IR (KBr): 1720, 1682, 1606, 1493 cm−1

A 11 tert-Butyl (3R,4R)-4-[4-(2-fluoro-3-methoxy-6-methoxy-methoxy-benzoyl)-benzoyloxy]-3-(3-methoxy-4-methoxymethoxy-benzoylamino)-azepane-1-carboxylate as a colourless foam from tert-butyl (3R,4R)-4-hydroxy-3-(3-methoxy-4-methoxymethoxy-benzoylamino)-azepane-1-carboxylate (B3) and 4-(2-fluoro-3-methoxy-6-methoxymethoxy-benzoyl)-benzoic acid (C3)
MS: m/e=741.6 (M+H)+
IR (KBr): 1720, 1683, 1600, 1493 cm−1

A 12 tert-Butyl (3R,4R)-4-[4-(2-fluoro-3-methoxy-6-methoxy-methoxy-benzoyl)-benzoyloxy]-3-(3,5-dimethoxy-4-methoxy-methoxy-benzoylamino)-azepane-1-carboxylate as a colourless foam from tert-butyl (3R,4R)-4-hydroxy-3-(3,5-dimethoxy-4-methoxymethoxy-benzoylamino)-azepane-1-carboxylate (B6) and 4-(2-fluoro-3-methoxy-6-methoxymethoxy-benzoyl)-benzoic acid (C3)
MS: m/e=771.6 (M+H)+
IR (KBr): 1721, 1679, 1586, 1493 cm−1

A 13 tert-Butyl 3R,4R)-4-[4-(2-fluoro-3-methoxy-6-methoxy-methoxy-benzoyl)-benzoyloxy]-3-(3,5-bis-methoxymethoxy-naphthalen-2-ylcarbonylamino)-azepane-1-carboxylate as a colourless foam from tert-butyl (3R,4R)-4-hydroxy-3-(3,5-bis-methoxymethoxy-naphthalen-2-ylcarbonylamino)-azepane-1-carboxylate (B7) and 4-(2-fluoro-3-methoxy-6-methoxymethoxy-benzoyl)-benzoic acid (C3)

A 14 tert-Butyl (3R,4R)-3-(3,5-dimethoxy-4-methoxymethoxy-benzoylamino)-4-[4-(3-methoxymethoxy-naphthalen-2-ylcarbonyl)-benzoyloxy]-azepane-1-carboxylate as a colourless foam from tert-butyl (3R,4R)-4-hydroxy-3-(3,5-dimethoxy-4-methoxymethoxy-benzoylamino)-azepane-1-carboxylate (B6) and 4-(3-methoxymethoxy-naphthalen-2-ylcarbonyl)-benzoic acid (C4)

A 15 tert-Butyl (3R,4R)-3-(3,5-dimethoxy-benzoylamino)-4-[4-(5-methoxy-2-methoxymethoxy-benzoyl)-benzoyloxy]-azepane-1-carboxylate als yellow foam from tert-butyl (3R,4R)-4-hydroxy-3-(3,5-dimethoxy-benzoylamino)-azepane-1-carboxylate (B8) and 4-(5-methoxy-2-methoxymethoxy-benzoyl)-benzoic acid (C7)
MS: 693.6 (M+H)+, 637.5, 605.4
IR: 3426, 1718, 1667, 1595, 1495, 1277, 1158, 840 cm−1

A 16 tert-Butyl (3R,4R)-4-[4-(2-fluoro-3-methoxy-6-methoxy-methoxy-benzoyl)-benzoyloxy]-3-(3-methoxy-2-methoxymethoxy-benzoylamino)-azepane-1-carboxylate as a colourless foam from tert-butyl (3R,4R)-4-hydroxy-3-(3-methoxy-2-methoxymethoxy-benzoylamino)-azepane-1-carboxylate (B9) and 4-(2-fluoro-3-methoxy-6-methoxymethoxy-benzoyl)-benzoic acid (C3)
MS: m/e=741.6 (M+H)+
IR (KBr): 1722, 1688, 1580, 1492 cm−1

A 17 tert-Butyl (3R,4R)-4-[4-(2-fluoro-3-methoxy-6-methoxy-methoxy-benzoyl)-benzoyloxy]-3-(3-methoxymethoxy-naphthalen-2-ylcarbonylamino)-azepane-1-carboxylate as a colourless foam from tert-butyl (3R,4R)-4-hydroxy-3-(3-methoxymethoxy-naphthalen-2-ylcarbonylamino)-azepane-1-carboxylate ((B10) and 4-(2-fluoro-3-methoxy-6-methoxymethoxy-benzoyl)-benzoic acid (C3)

A 18 tert-Butyl (3R,4R)-3-(4-methoxymethoxy-benzoylamino)-4-[4-(3-methoxymethoxy-5,6,7,8-tetrahydro-naphthalen-2-ylcarbonyl)-benzoyloxy]-azepane-1-carboxylate as a colourless foam from tert-butyl (3R,4R)-4-hydroxy-3-(4-methoxymethoxy-benzoylamino)-azepane-1-carboxylate (B2) and 4-(3-methoxymethoxy-5,6,7,8-tetrahydro-naphthalen-2-ylcarbonyl)-benzoic acid (C8)

A 19 tert-Butyl (3R,4R)-4-[4-(2-fluoro-3-methoxy-6-benzoyl)-benzoyloxy]-3-(3,5-dimethoxy-benzoylamino)-azepane-1-carboxylate as a colourless foam from tert-butyl (3R,4R)-4-hydroxy-3-(3,5-dimethoxy-benzoylamino)-azepane-1-carboxylate (B8) and 4-(2-fluoro-3-methoxy-6-methoxymethoxy-benzoyl)-benzoic acid ((C3)

MS:709.6 (M–H)⁻
IR: 3414, 1721, 1676, 1594, 1528, 1491, 1272, 1157, 1039 cm⁻¹

A 20 tert-Butyl (3R,4R)-4-[4-(2-fluoro-3-methoxy-6-methoxy-methoxy-benzoyl)-benzoyloxy]-3-(4-methoxymethoxy-2,3,6-trimethyl-benzoylamino)-azepane-1-carboxylate as a colourless foam from tert-butyl (3R,4R)-4-hydroxy-3-(4-methoxymethoxy-2,3,6-trimethyl-benzoyl-amino)-azepane-1-carboxylate (B11) and 4-(2-fluoro-3-methoxy-6-methoxymethoxy-benzoyl)-benzoic acid (C3)
MS: m/e=753.5 (M+H)⁺
IR (KBr): 1721, 1686, 1587, 1491 cm⁻¹

A 21 tert-Butyl (3R,4R)-4-[4-(2,3-difluoro-6-methoxymethoxy-benzoyl)-benzoyloxy]-3-(4-methoxymethoxy-2,3,6-trimethyl-benzoylamino)-azepane-1-carboxylate as a colourless foam from tert-butyl (3R,4R)-4-hydroxy-3-(4-methoxymethoxy-2,3,6-trimethyl-benzoylamino)-azepane-1-carboxylate (B11) and 4-(2,3-difluoro-6-methoxymethoxy-benzoyl)-benzoic acid (C5)
MS: m/e=741.5 (M+H)⁺
IR (KBr): 1722, 1688, 1580, 1492 cm⁻¹

A 22 tert-Butyl (3R,4R)-4-[4-(2,3-difluoro-6-methoxymethoxy-benzoyl)-benzoyloxy]-3-(3,5-diisopropyl-4-methoxymethoxy-benzoylamino)-azepane-1-carboxylate as a colourless foam from tert-butyl (3R, 4R)-4-hydroxy-3-(3,5-diisopropyl-4-methoxy-methoxy-benzoyl-amino)-azepane- 1-carboxylate (B12) and 4-(2,3-difluoro-6-methoxymethoxy-benzoyl)-benzoic acid (C5)
MS: m/e =783.6 (M+H)⁺
IR (KBr): 1722, 1680, 1602, 1492 cm⁻¹

A 23 tert-Butyl (3R,4R)-4-[4-(5-methoxy-2-methoxymethoxy-benzoyl)-benzoyloxy]-3-(3,4,5-trimethoxy-benzoylamino)-azepane-1-carboxylate as a yellow foam from tert-butyl (3R,4R)-4-hydroxy-3-(3,4,5-trimethoxy-benzoylamino)-azepane-1-carboxylate (B13) and 4-(5-methoxy-2-methoxymethoxy-benzoyl)-benzoic acid (C7)
MS: 723.6 (M+H)⁺, 667.5
IR: 3422, 1720, 1696, 1666, 1586, 1497, 1278, 1235, 1127, 990, 841 cm⁻¹

A 24 tert-Butyl (3R,4R)-4-[4-(5-dimethylamino-2-methoxy-methoxy-benzoyl)-benzoyloxy]-3-(4-methoxymethoxy-benzoyl-amino)-azepane-1-carboxylate as an orange foam from tert-butyl (3R,4R)-4-hydroxy-3-(4-methoxymethoxy-benzoylamino)-azepane-1-carboxylate (B2) and 4-(5-dimethylamino-2-methoxymethoxy-benzoyl)-benzoic acid (C9)
MS: m/e=706.6 (M+H)⁺
IR (KBr): 1719, 1665, 1606, 1502 cm⁻¹

A 25 tert-Butyl (3R,4R)-3-(3-methoxy-4-methoxymethoxy-benzoylamino)-4-[4[-(2-methoxymethoxy-5-dimethylamino-benzoyl)-benzoyloxy]-azepane-1-carboxylate as an orange foam from tert-butyl (3R,4R)-4-hydroxy-3-(3-methoxy-4-methoxymethoxy-benzoylamino)-azepane-1-carboxylate (B3) and 4-(5-dimethylamino-2-methoxymethoxy-benzoyl)-benzoic acid (C9)
MS: m/e=736.6 (M+H)⁺
IR (KBr): 1718, 1665, 1605, 1504 cm⁻¹

A 26 tert-Butyl (3R,4R)-3-(3,5-diisopropyl-4-methoxymethoxy-benzoylamino)-4-[4-(2-methoxymethoxy-5-dimethylamino-benzoyl)-benzoyloxy]-azepane-1-carboxylate as an orange foam from tert-butyl (3R,4R)-4-hydroxy-3-(3,5-diisopropyl-4-methoxy-methoxy-benzoyl-amino)-azepane-1-carboxylate (B12) and 4-(2-methoxymethoxy-5-dimethylamino-benzoyl)-benzoic acid (C9)
MS: m/e=790.7 (M+H)⁺;
IR (KBr): 1719, 1666, 1605, 1503 cm⁻¹

A 27 tert-Butyl (3R,4R)-4-[4-(2,3-dihydro-1,4-benzodioxin-6-ylcarbonyl)-benzoyloxy]-3-(4-methoxymethoxy-benzoylamino)-azepane-1-carboxylate as a colourless foam from tert-butyl (3R,4R)-4-hydroxy-3-(4-methoxymethoxy-benzoylamino)-azepane-1-carboxylate (B2) and 4-(7-methoxymethoxy-2,3-dihydro-1,4-benzodioxin-6-ylcarbonyl)benzoic acid (C10)

A 28 tert-Butyl (3R,4R)-4-[4-[5-(1-methoxyethyl)-2-methoxy-methoxy-benzoyl]-benzoyloxy-3-(4-methoxymethoxy-benzoyl-amino)-azepane-1-carboxylate as a colourless foam from tert-butyl (3R,4R)-4-hydroxy-3-(4-methoxymethoxy-benzoylamino)-azepane-1-carboxylate (B2) and (RS)-4-[5-(1-methoxyethyl)-2-methoxymethoxy-benzoyl]-benzoic acid (c11)

A 29 tert-Butyl (3R,4R)-4-[4-(2-fluoro-3-methoxy-6-methoxy-methoxy-benzoyl)-benzoyloxy]-3-(4-methoxymethoxy-3,5-dimethyl-benzoylamino)-azepane-1-carboxylate as a colourless foam from tert-butyl (3R, 4R)-4-hydroxy-3-(4-methoxymethoxy-3,5-dimethyl-benzoylamino)-azepane-1-carboxylate (B14) and 4-(2-fluoro-3-methoxy-6-methoxymethoxy-benzoyl)-benzoic acid (C3)
MS: m/e=739.7 (M+H)⁺;
IR (KBr): 1721, 1677, 1503 cm⁻¹

A 30 tert-Butyl (3R,4R)-4-[4-(2-methoxymethoxy-5-dimethyl-amino-benzoyl)-benzoyloxy]-3-(4-methoxymethoxy-3,5-dimethyl-benzoylamino)-azepane-1-carboxylate as an orange foam from tert-butyl (3R,4R)-4-hydroxy-3-(4-methoxymethoxy-3,5-dimethyl-benzoylamino)-azepane-1-carboxylate (B14) and 4-(2-methoxymethoxy-5-dimethylamino-benzoyl)-benzoic acid (C9)
MS: m/e=734.9 (M+H)⁺
IR (KBr): 1719, 1666, 1606, 1503 cm⁻¹

A 31 tert-Butyl (3R,4R)-4-[4-(2-fluoro-4-methoxy-6-methoxy-methoxy-benzoyl)-benzoyloxy]-3-(3,5-diisopropyl-4-methoxy-methoxy-benzoylamino)-azepane-1-carboxylate as a colourless foam from tert-butyl (3R,4R)-4-hydroxy-3-(3,5-diisopropyl-4-methoxymethoxy-benzoyl-amino)-azepane-1-carboxylate (B12) and 4-(2-fluoro-4-methoxy-6-methoxymethoxy-benzoyl)-benzoic acid (C1)
MS: m/e=795.6 (M+H)⁺
IR (KBr): 1720, 1669, 1622, 1581, 1528 cm⁻¹

A 32 tert-Butyl (3R,4R)-3-(3-acetyl-4-methoxymethoxy-benzoyl-amino)-4-[4-(5-methoxy-2- methoxymethoxy-benzoyl)-benzoyloxy]-azepane-1-carboxylate as a yellow foam from tert-butyl (3R,4R)-3-(3-acetyl-4-methoxymethoxy-benzoylamino)-4-hydroxy-azepane-1-carboxylate (B15) and 4-(5-methoxy-2-methoxymethoxy-benzoyl)-benzoic acid (C7)
MS: 735.6 (M+H)⁺, 679.5
IR: 3450, 1719, 1671, 1603, 1491, 1277, 1156, 981 cm⁻¹

A 33 tert-Butyl (3R,4R)-3-(4-methoxymethoxy-benzoylamino)-4-[4-(6-methoxymethoxy-quinolin-7-ylcarbonyl)-benzoyloxy]-azepane-1-carboxylate as a yellow foam from tert-butyl (3R,4R)-4-hydroxy-3-(4-methoxymethoxy-benzoylamino)-azepane-1-carboxylate (B2) and 4-(6-methoxymethoxy-quinolin-7-ylcarbonyl)-benzoic acid (C12)

A 34 tert-Butyl (3R,4R)-4-[4-(2,3-difluoro-6-methoxymethoxy-benzoyl)-benzoyloxy)-3-(4- methoxymethoxy-3,5-dimethyl-benzoyl-amino)-azepane-1-carboxylate as a colourless foam from tert-butyl (3R,4R)-4-hydroxy-3-(4-methoxymethoxy-3,5-dimethyl-benzoylamino)-azepane-1-carboxylate (B14) and 4-(2,3-difluoro-6-methoxymethoxy-benzoyl)-benzoic acid (C5)
MS: m/e=727.5 (M+H)⁺
IR (KBr): 1721, 1683, 1603, 1491 cm⁻¹

A 35 tert-Butyl (3R,4R)-4-[4-(2,4-difluoro-6-methoxymethoxy-benzoyl)-benzoyloxy]-3-(4-methoxymethoxy-3,5-dimethyl-benzoyl-amino)-azepane-1-carboxylate as a colourless foam from tert-butyl (3R,4R)-4-hydroxy-3-(4-methoxymethoxy-3,5-dimethyl-benzoylamino)-azepane-1-carboxylate (B14) and 4-(2,4-difluoro-6-methoxymethoxy-benzoyl)-benzoic acid (C6)
MS: m/e=727.5 (M+H)⁺
IR (KBr): 1721, 1675, 1620, 1603, 1482 cm⁻¹

A 36 tert-Butyl (3R,4R)-3-(3,5-diethoxy-benzoylamino)-4-[4-(5-methoxy-2-methoxymethoxy-benzoyl)-benzoyloxy]-azepane-1-carboxylate as a yellow foam from tert-butyl (3R,4R)-3-(3,5-diethoxy-benzoylamino)-4-hydroxy-azepane-1-carboxylate (B16) and 4-(5-methoxy-2-methoxymethoxy-benzoyl)-benzoic acid (C7)
MS: 721.5 (M+H)⁺, 665.5, 585.4, 409.3
IR: 3429, 1719, 1667, 1593, 1495, 1276, 1172, 990 cm⁻¹

A 37 tert-Butyl (3R,4R)-3-(4-methoxymethoxy-benzoylamino)-4-[4-(4-methoxymethoxy-biphenyl-3-ylcarbonyl)-benzoyloxy]-azepane-1-carboxylate as a yellow foam from tert-butyl (3R,4R)-4-hydroxy- 3-(4-methoxymethoxy-benzoylamino)-azepane-1-carboxylate (B2) and 4-(4-methoxymethoxy-biphenyl-3-ylcarbonyl)-benzoic acid (C13)

A 38 tert-Butyl (3R,4R)-3-(4-methoxymethoxy-3,5-dimethyl-benzoylamino)-4-[4-(6-methoxymethoxy-quinolin-7-ylcarbonyl)-benzoyloxy]-azepane-1-carboxylate as a yellow foam from tert-butyl (3R,4R)-4-hydroxy-3-(4-methoxymethoxy-3,5-dimethyl-benzoylamino)-azepane-1-carboxylate (B14) and 4-(6-methoxymethoxy-quinolin-7-ylcarbonyl)-benzoic acid (c 12)

A 39 tert-Butyl (3R,4R)-4-[4-(5-acetyl-2-methoxymethoxy-benzoyl)-benzoyloxy]-3-(4-methoxymethoxy-benzoylamino)-azepane-1-carboxylate as a yellow foam from tert-butyl (3R,4R)-4-hydroxy-3-(4-methoxymethoxy-benzoylamino)-azepane-1-carboxylate (B2) and 4-(5-acetyl-2-methoxymethoxy-benzoyl)-benzoic acid (C14)

A 40 tert-Butyl (3R,4R)-3-(4-methoxymethoxy-benzoylamino4-[3-methoxymethoxy-10-methyl-phenothiazin-2-ylcarbonyl)-benzoyl]-azepane-1-carboxylate as a yellow foam from tert-butyl (3R,4R)-4-hydroxy-3-(4-methoxymethoxy-benzoylamino)-azepane-1-carboxylate (B2) and 4-(3-methoxymethoxy-10-methyl-phenothiazin-2-ylcarbonyl)-benzoic acid (C15)
MS: 798.6 (M+H)⁺
IR: 2840, 1718,1693, 1603, 1536, 1501, 1265, 1153, 847, 752.

A 41 tert-Butyl (3R,4R)-3-(3,5-diethyl-4-methoxymethoxy-benzoylamino)-4-[2-fluoro-3-methoxy-6-methoxymethoxy-benzoyl)-benzoyloxy]-azepane-1-carboxylate as a colourless foam from tert-butyl (3R,4R)-3-(3,5-diethyl-4-methoxymethoxy-benzoylamino)-4-hydroxy-azepane-1-carboxylate (B17) and 4-(2-fluoro-3-methoxy-6-methoxymethoxy-benzoyl)-benzoic acid (C3)
MS: m/e=767.6 (M+H)⁺
IR (KBr): 1721, 1672, 1585, 1491 cm⁻¹

A 42 tert-Butyl (3R,4R)-3-(3,5-diethyl-4-methoxymethoxy-benzoylamino)-4-[4-(2,3-difluoro-6-methoxymethoxy-benzoyl)-benzoyloxy]-azepane-1-carboxylate as a colourless foam from tert-butyl (3R,4R)-3-(3,5-diethyl-4-methoxymethoxy-benzoylamino)-4-hydroxy-azepane-1-carboxylate (B17) and 4-(2,3-difluoro-6-methoxymethoxy-benzoyl)-benzoic acid (C5)
MS: m/e=755.6 (M+H)⁺
IR (KBr): 1721, 1684, 1603, 1492 cm⁻¹

A 43 tert-Butyl (3R,4R)-3-(3,5-diethyl-4-methoxymethoxy-benzoylamino)-4-[4-(2-methoxymethoxy-5-dimethylamino-benzoyl)-benzoyloxy]-azepane-1-carboxylate as an orange foam from tert-butyl (3R,4R)-3-(3,5-diethyl-4-methoxymethoxy-benzoylamino)-4-hydroxy-azepane-1-carboxylate (B17) and 4-(2-methoxymethoxy-5-dimethylamino-benzoyl)-benzoic acid (C9)
MS: m/e=762.7 (M+H)⁺
IR (KBr): 1719, 1666, 1606, 1503 cm⁻¹

A 44 tert-Butyl (3R,4R)-3-(3,5-diethyl-4-methoxymethoxy-benzoylamino)-4-[4-(2,4-difluoro-6-methoxymethoxy-benzoyl)-benzoyloxy]-azepane-1-carboxylate as a colourless foam from tert-butyl (3R,4R)-3-(3,5-diethyl-4-methoxymethoxy-benzoylamino)-4-hydroxy-azepane-1-carboxylate (B17) and 4-(2,4-difluoro-6-methoxymethoxy-benzoyl)-benzoic acid [(C6)
MS: m/e=755.6 (M+H)⁺
IR (KBr): 1720, 1674, 1619, 1464 cm⁻¹

A 45 tert-Butyl (3R,4R)-4-[4-(5-methoxy-2-methoxymethoxy-benzoyl)-benzoyloxy]-3-(4-methoxymethoxy-3,5-dimethyl-benzoylamino)-azepane-1-carboxylate from tert-butyl (3R,4R)-4-hydroxy-3-(4-methoxymethoxy-3,5-dimethyl-benzoylamino)-azepane-1-carboxylate (B14) and 4-(5-methoxy-2-methoxy-methoxy-benzoyl)-benzoic acid (C7)

A 46 tert-Butyl (3R,4R)-4-[4-(5-methoxy-2-methoxymethoxy-benzoyl)-benzoyloxy]-3-(4-pyridinoylamino)-azepane-1-carboxylate as a yellow foam from tert-butyl (3R,4R)-4-hydroxy-3-(4-pyridinoylamino)-azepane-1-carboxylate (B22) and 4-(5-methoxy-2-methoxymethoxy-benzoyl)-benzoic acid (C7)
MS: 634.4 (M+H)⁺, 578.4;
IR: 3390, 1720, 1671, 1532, 1493, 1276, 1159, 991 cm⁻¹

A 47 tert-Butyl (3R,4R)-3-(4-methoxymethoxy-benzoylamino)-4-[4-(2-methoxymethoxy-5-methyl-benzoyl)-benzoyloxy]-azepane-1-carboxylate as a white solid from tert-butyl (3R,4R)-4-hydroxy-3-(4-methoxymethoxy-benzoylamino)-azepane-1-carboxylate (B2) and 4-(2-methoxymethoxy-5-methyl-benzoyl)-benzoic acid (C16).
M.p.=66.2° C.
MS: 677.3 (M+H)⁺, 621.2, 577.3
IR: 3430, 2788, 1719, 1690, 1665, 1606, 1500, 1279, 994.

A 48 tert-Butyl (3R,4R)-4-[4-(6-methoxymethoxy-1,3-benzodioxol-5-ylcarbonyl)-benzoyloxy]-3-(4-methoxymethoxy-3,5-dimethyl-benzoylamino)-azepane-1-carboxylate as a colourless foam from tert-butyl (3R, 4R)-4-hydroxy-3-(4-methoxymethoxy-3,5-dimethyl-benzoylamino)-azepane-1-carboxylate (B14) and 4-(6-methoxymethoxy-1,3-benzodioxol-5-ylcarbonyl)-benzoic acid (C17)

A 49 tert-Butyl (3R,4R)-4-[4-(5-isopropyl-2-methoxymethoxy-benzoyl)-benzoyloxy]-3-(4-methoxymethoxy-benzoylamino)-azepane-1-carboxylate as a colourless foam from tert-butyl (3R,4R)-4-hydroxy-3-(4-methoxymethoxy-benzoylamino)-azepane-1-carboxylate (B2) and 4-(5-isopropyl-2-methoxymethoxy-benzoyl)-benzoic acid (C18)

MS: 705.5 (M+H)+, 649.5

IR 3405, 1719, 1666, 1535, 1499, 1278, 1239, 1154, 994,840

Anal. calc. for $C_{39}H_{48}N_2O_{10}$ (704.817); C 66.46, H 6.86, N 3.97; found : C 66.27, H 6.97, N 3.74.

A 50 tert-Butyl (3R,4R)-4-[4-(6-methoxymethoxy-(1,4-benzodioxin-5-ylcarbonyl)-benzoyloxy]-3-(4-methoxymethoxy-3,5-dimethyl-benzoylamino)-azepane-1-carboxylate as a yellow solid from tert-butyl (3R,4R)-4-hydroxy-3-(4-methoxymethoxy-3,5-dimethyl-benzoylamino)-azepane-1-carboxylate (B14) and 4-(6-methoxymethoxy-1,4-benzodioxin-5-ylcarbonyl)-benzoic acid (C19)

MS: 749.5 (M+H)+, 693.4

IR.: 3428, 7120, 1672, 1602, 1529, 1268, 1157, 1098, 1021.

A 51 tert-Butyl (3R,4R)-4-[4-(2-fluoro-3-dimethylamino-6-methoxymethoxy-benzoyl)-benzoyloxy]-3-(4-methoxymethoxy-benzoylamino)-azepane-1-carboxylate as a yellow foam from tert-butyl (3R,4R)-4-hydroxy-3-(4-methoxymethoxy-benzoylamino)-azepane-1-carboxylate (B2) and 4-(2-fluoro-3-dimethylamino-6-methoxymethoxy-benzoyl)-benzoic acid (C20)

MS: m/e=724.5 (M+H)+

IR (KBr): 1720, 1680, 1606, 1498 cm$^{-1}$

A 52 tert-Butyl (3R,4R)-4-[4-(2-fluoro-3-dimethylamino-6-methoxymethoxy-benzoyl)-benzoyloxy]-3-(4-methoxymethoxy-3,5-dimethyl-benzoylamino)-azepane-1-carboxylate as a yellow foam from tert-butyl (3R,4R)-4-hydroxy-3-(4-methoxymethoxy-3,5-dimethyl-benzoylamino)-azepane-1-carboxylate (B14) and 4-(2-fluoro-3-dimethylamino-6-methoxymethoxy-benzoyl)-benzoic acid (C20)

MS: m/e=752.5 (M+H)+

IR (KBr): 1721, 1672, 1608, 1490 cm$^{-1}$

A 53 tert-Butyl (3R,4R)-4-[4-(2-fluoro-3-dimethylamino-6-methoxymethoxy-benzoyl)-benzoyloxy]-3-(3,5-dimethoxy-4-methoxymethoxy-benzoylamino)-azepane-1-carboxylate as a yellow foam from tert-butyl (3R,4R)-4-hydroxy-3-(3,5-dimethoxy-4-methoxymethoxy-benzoylamino)-azepane-1-carboxylate (B6) and 4-(2-fluoro-3-dimethylamino-6-methoxymethoxy-benzoyl)-benzoic acid (C20)

MS: m/e=784.5 (M+H)+

IR (KBr): 1721, 1673, 1587, 1495 cm$^{-1}$

A 54 tert-Butyl (3R,4R)-4-[4-(5-acetyl-2-methoxymethoxy-benzoyl)-benzoyloxy)-3-(4-methoxymethoxy-3,5-dimethyl-benzoylamino)-azepane-1-carboxylate as a yellow foam from tert-butyl (3R,4R)-4-hydroxy-3-(4-methoxymethoxy-3,5-dimethyl-benzoylamino)-azepane-1-carboxylate (B14) and 4-(5-acetyl-2-methoxymethoxy-benzoyl)-benzoic acid (C14)

A 55 tert-Butyl (3R,4R)-4-[4-(2-fluoro-3-methoxy-6-methoxy-methoxy-benzoyl)-benzoyloxy]-3-(4-pyridinoylamino)-azepane-1-carboxylate as a colourless foam from tert-butyl (3R,4R)-4-hydroxy-3-(4-pyridinoylamino)-azepane-1-carboxylate (B22) and 4-(2-fluoro-3-methoxy-6-methoxymethoxy-benzoyl)-benzoic acid (C3)

MS: 652.5 (M+H)+, 596.3

IR: 3340, 1729, 1679, 1532, 1491, 1282, 1157, 821, 749 cm$^{-1}$

A 56 tert-Butyl (3R,4R)-3-(3-tert-Butyl-4-hydroxy-benzoylamino)-4-[4-(5-methoxy-2-methoxymethoxy-benzoyl)-benzoyloxy]-azepane-1-carboxylate as a white solid from tert-butyl (3R,4R)-3-(3-tert-butyl-4-hydroxy-benzoylamino)-4-hydroxy-azepane-1-carboxylate (B18) and 4-(5-methoxy-2-methoxymethoxy-benzoyl)-benzoic acid (C7)

MS: 705.5 (M+H)+, 649.5

IR: 3426, 1742, 1665, 1537, 1489, 1259, 1193, 1158, 988 cm$^{-1}$

A 57 tert-Butyl (3R,4R)-3-(3-bromo-4-methoxymethoxy-benzoyl-amino)-4-[4-(2-fluoro-3-methoxy-6-methoxymethoxy-benzoyl)-benzoyloxy]-azepane-1-carboxylate as a yellow foam from tert-butyl (3R,4R)-3-(3-bromo-4-methoxymethoxy-benzoylamino)-4-hydroxy-azepane-1-carboxylate (B19) and 4-(2-fluoro-3-methoxy-6-methoxymethoxy-benzoyl)-benzoic acid (C3)

A 58 tert-Butyl (3R,4R)-3-(3-isopropyl-4-methoxymethoxy-benzoylamino)-4-[4-(5-methoxy-2-methoxymethoxy-benzoyl)-benzoyloxy]-azepane-1-carboxylate as a yellow foam from tert-butyl (3R,4R)-4-hydroxy-3-(3-isopropyl-4-methoxymethoxy-benzoylamino)-azepane-1-carboxylate (B20) and 4-(5-methoxy-2-methoxymethoxy-benzoyl)-benzoic acid (C7)

MS: 735.5 (M+H)+, 679.5

IR: 3432, 1719, 1666, 1532, 1493, 1277, 1151, 994 cm$^{-1}$

A 59 tert-Butyl (3R,4R)-3-(3-sec-butyl-4-methoxymethoxy-benzoylamino)-4-[4-(5-methoxy-2-methoxymethoxy-benzoyl)-benzoyloxy]-azepane-1-carboxylate as a yellow foam from tert-butyl (3R,4R)-3-(3-sec-butyl-4-methoxymethoxy-benzoylamino)-4-hydroxy-azepane-1-carboxylate (B21) and 4-(5-methoxy-2-methoxymethoxy-benzoyl)-benzoic acid (C7)

MS: 749.5 (M+H)+, 693.4

IR: 3443, 1720, 1666, 1532, 1493, 1277, 1150, 995 cm$^{-1}$

A 60 tert-Butyl (3R,4R)-4-[4-(2-fluoro-3-isopropyl-6-methoxy-methoxy-benzoyl)-benzoyloxy ]-3-(4-methoxymethoxy-3,5-dimethyl-benzoylamino)-azepane-1-carboxylate as a yellow foam from tert-butyl (3R,4R)-4-hydroxy-3-(4-methoxymethoxy-3,5-dimethyl-benzoylamino)-azepane-1-carboxylate (B14) and 4-(2-fluoro-3-isopropyl-6-methoxymethoxy-benzoyl)-benzoic acid (C2)

A 61 tert-Butyl (3R,4R)-4-[4-(2-fluoro-6-methoxymethoxy-3-pyrrolidin-1-yl-benzoyl)-benzoyloxy]-3-(4-methoxymethoxy-benzoylamino)-azepane-1-carboxylate as an orange foam from tert-butyl (3R,4R)-4-hydroxy-3-(4-methoxymethoxy-benzoylamino)-azepane-1-carboxylate (B2) and 4-(2-fluoro-6-methoxymethoxy-pyrrolidin-1-yl-benzoyl)-benzoic acid (C22)

M:MS: m/e=750.7 (M+H)+

IR (KBr): 1721, 1683, 1574, 1499 cm$^{-1}$

A 62 tert-Butyl (3R,4R)-4-[4-(2-fluoro-6-methoxymethoxy-3-pyrrolidin-1-yl-benzoyl)-benzoyloxy]-3-(4-methoxymethoxy-3,5-dimethyl-benzoylamino)-azepane-1-carboxylate as an orange foam from tert-butyl (3R,4R)-4-hydroxy-3-(4-methoxymethoxy-3,5-dimethyl-benzoylamino)-azepane-1-carboxylate (B14) and 4-(2-fluoro-6-methoxymethoxy-pyrrolidin-1-yl-benzoyl)-benzoic acid (C22)

MS: m/e=778.6 (M+H)+

IR (KBr): 1721, 1675, 1603, 1486 cm$^{-1}$

A 63 tert-Butyl (3R,4R)-3-(4-methoxymethoxy)-benzoylamino)-4 [4-(2-fluoro-6-methoxymethoxy-3-methyl-benzoyl)-benzoyloxy]-azepane-1-carboxylate as a colourless oil from tert-butyl (3R,4R)- 4-hydroxy-3-(4-methoxymethoxy-benzoylamino)-azepane-1-carboxylate (B2) and 4-(2-fluoro-6-methoxymethoxy-3-methyl-benzoyl)-benzoic acid (C23)

MS 695.5 (M+H)+, 639.5

IR: 3380, 2934, 1719, 1671, 1613, 1605, 1535, 1500, 1241, 1153, 993, 895.

Anal. calc. for $C_{37}H_{43}N_2O_{10}F$ (694.753): C 63.97, 6.24, 4.03; found C 63.69, 6.57, 3.73.

A 64 tert-Butyl (3R,4R)-4-[4-(3-ethyl-2-fluoro-6-methoxy-methoxy-benzoyl)-benzoyloxy]-3-(4-methoxymethoxy-3,5-dimethyl-benzoylamino)-azepane-1-carboxylate as a colourless oil from tert-butyl (3R,4R)-4-hydroxy-3-(4-methoxymethoxy-3,5-dimethyl-benzoylamino)-azepane-1-carboxylate (B14) and 4-(3-ethyl-2-fluoro-6-methoxymethoxy-benzoyl)-benzoic acid (C24)

MS: 737.5 (M+H)⁺, 681.5

IR: 3335, 1720, 1682, 1530, 1269, 1158, 1095, 1036.

A 65 tert-Butyl (3R,4R)-4-[4-(2-fluoro-6-methoxymethoxy-3-piperidin-1-yl-benzoyl)-benzoyloxy]-3-(4-methoxymethoxy-benzoylamino)-azepane-1-carboxylate as an orange foam from tert-butyl (3R,4R)-4-hydroxy-3-(4-methoxymethoxy-benzoylamino)-azepane-1-carboxylate (B14) and 4-(2-fluoro-6-methoxymethoxy-piperidin-1-yl-benzoyl)-benzoic acid (C25)

MS: m/e=792.6 (M+H)⁺

IR (KBr): 1721, 1683, 1604, 1573, 1530, 1486, 1269, 1158, 1038, 971 cm⁻¹

Example B

B. The alcohols used in Example A were prepared by:
method a) hydrogenolytic cleavage of alcohol protecting groups from corresponding protected compounds; or
method b) acylation of a corresponding amine with a carboxylic acid or an acetone oxime ester The following compounds were obtained:

B 1 (Method a) tert-butyl (3R,4R)-3-[4-[dimethyl(1,1,2-trimethyl-propyl)siloxy]-benzoylamino)-4-hydroxy-azepane-1-carboxylate as a colourless foam from tert-butyl (3R,4R)-4-benzyloxy-3-[4-[dimethyl-(1,1,2-trimethylpropyl)-siloxy]benzoylamino]-azepane-1-carboxylate (R2)

MS:493 (M+H)⁺, 437, 393, 263

IR: 3421, 1692, 1667, 1604, 1501, 1264, 1171, 911 cm⁻¹

B 2 (Method a) tert-Butyl (3R,4R)-4-hydroxy-3-(4-methoxy-methoxy-benzoyl-amino)-azepane-1-carboxylate as a colourless foam from tert-butyl (3R,4R)-4-benzyloxy-3-(4-methoxymethoxy-benzoyl-amino)-azepane-1-carboxylate (R1)

MS: m/e=395 (M+H)⁺

IR (flm): 3341, 1688, 1665, 1636, 1606, 1541, 1155, 1079 cm⁻¹

B 3 (Method a) tert-Butyl (3R,4R)-4-hydroxy-3-(3-methoxy-4-methoxymethoxy-benzoylamino)-azepane-1-carboxylate as a colourless foam from tert-butyl (3R,4R)-4-benzyloxy-3-(3-methoxy-4-methoxymethoxy-benzoylamino)-azepane-1-carboxylate (R3)

MS: m/e=425.2 (M+H)⁺

IR (KBr): 3369, 1690, 1664, 1638, 1605, 1544, 1162, 1077 cm⁻¹

B 4 (Method a) tert-Butyl (3R,4R)-4-hydroxy-3-(5-methoxy-2-methoxymethoxy-benzoylamino)-azepane-1-carboxylate as a colourless foam from tert-butyl (3R,4R)-4-benzyloxy-3-(5-methoxy-2-methoxymethoxy-benzoylamino)-azepane-1-carboxylate (R4)

B 5 (Method a) tert-Butyl (3R,4R)-3-[4-(tert-butyldimethyl-silanyloxy)-benzoylamino]-4-hydroxy-azepane-1-carboxylate as a colourless foam from tert-butyl (3R,4R)-4-benzyloxy-3-[4-(tert-butyldimethylsilanyloxy)-benzoylamino]-azepane-1-carboxylate (R5) B 6 (Method a) tert-Butyl (3R,4R)-4-hydroxy-3-(3,5-dimethoxy-4-methoxymethoxy-benzoylamino)-azepane-1-carboxylate as a colourless foam from tert-butyl (3R,4R)-4-benzyloxy-3-(3,5-dimethoxy-4-methoxymethoxy-benzoylamino)-azepane-1-carboxylate (R6)

MS: m/e=455 (M+H)⁺

IR (KBr): 3378, 1693, 1663, 1640, 1587, 1543, 1162, 1079 cm⁻¹

B 7 (Method a) tert-Butyl (3R,4R)-4-hydroxy-3-(3,5-bis-methoxy-methoxy-naphthalen-2-ylcarbonylamino)-azepane-1-carboxylate as a colourless foam from tert-butyl (3R,4R)-4-benzyloxy-3-(3,5-bis-methoxymethoxy-naphthalen-2-ylcarbonylamino)-azepane-1-carboxylate (R7)

B 8 (Method a) tert-Butyl (3R,4R)-4-hydroxy-3-(3,5-dimethoxy-benzoylamino)-azepane-1-carboxylate as a colourless foam from tert-butyl (3R,4R)-4-benzyloxy-3-(3,5-dimethyl-benzoylamino)-azepane-1-carboxylate (R8)

MS:395 (M+H)⁺

IR: 3335, 1664, 1594, 1536, 1156, 1064 cm⁻¹

B 9 (Method a) tert-Butyl (3R,4R)-4-hydroxy-3-(3-methoxy-2-methoxymethoxy-benzoyl-amino)-azepane-1-carboxylate as a colourless foam from tert-butyl (3R,4R)-4-benzyloxy-3-(3-methoxy-2-methoxymethoxy-benzoyl-amino)-azepane-1-carboxylate (R9)

MS: m/e=368 (M-C₄H₈)⁺

IR (flm): 3376, 1687, 1660, 1578, 1527, 1163, 1077 cm⁻¹

B 10 (Method a) tert-Butyl (3R,4R)-4-hydroxy-3-(3-methoxy-methoxy-naphthalen-2-ylcarbonylamino)-azepane-1-carboxylate as a colourless foam from tert-butyl (3R,4R)-4-benzyloxy-3-(3-methoxymethoxy-naphthalen-2-ylcarbonylamino)-azepane-1-carboxylate (R10)

IR: 3335, 1664, 1594, 1536, 1156, 1064 cm⁻¹

B 11 (Method a) tert-Butyl (3R,4R)-4-hydroxy-3-(4-methoxy-methoxy-2,3,6-trimethyl-benzoyl-amino)-azepane-1-carboxylate as a colourless foam from tert-butyl (3R,4R)-4-benzyloxy-3-(4-methoxymethoxy-2,3,6-trimethyl-benzoyl-amino)-azepane-1-carboxylate (R11)

MS: m/e=437.6 (M+H)⁺

IR (KBr): 3402, 1692, 1673, 1638, 1597, 1533, 1160, 1054 cm⁻¹

B 12 (Method a) tert-Butyl (3R,4R)-4-hydroxy-3-(3,5-diisopropyl-4-methoxymethoxy-benzoyl-amino)-azepane-1-carboxylate [Ro 47–61431] as a colourless foam from tert-butyl (3R,4R)-4-benzyloxy-3-(3,5-diisopropyl-4-methoxymethoxy-benzoyl-amino)-azepane-1-carboxylate (R12)

MS: m/e=479.6 (M+H)⁺

IR (KBr): 3426, 1695, 1665, 1640, 1603, 1537, 1162, 1071 cm⁻¹

B 13 (Method a) tert-Butyl (3R,4R)-4-hydroxy-3-(3,4,5-trimethoxy-benzoylamino)-azepane-1-carboxylate as a colourless powder from tert-butyl (3R,4R)-4-benzyloxy-3-(3,4,5-trimethoxy-benzoylamino)azepane-1-carboxylate (R13)

MS:447.6 (M+H)⁺, 425.6, 369.5, 325.4

IR: 3381, 1664, 1583, 1546, 1237, 1172, 1126, 1010 cm⁻¹

B 14 (Method a) tert-Butyl (3R,4R)-4-hydroxy-3-(4-methoxy-methoxy-3,5-dimethyl-benzoylamino)-azepane-1-carboxylate as a colourless foam from tert-butyl (3R,4R)-benzyloxy-3-(4-methoxymethoxy-3,5-dimethyl-benzoylamino)-azepane-1-carboxylate (R14)

MS: m/e=423.4 (M+H)⁺

IR (flm): 3339, 1695, 1665, 1640, 1602, 1536, 1162, 1073 cm⁻¹

B 15 (Method a) tert-Butyl (3R,4R)-3-(3-acetyl-4-methoxy-methoxy-benzoylamino)4-hydroxy-azepane-1-carboxylate as a colourless foam from tert-butyl (3R,4R)-3-(3-acetyl-4-methoxy-methoxy-benzoylamino)4-benzyloxy-azepane-1-carboxylate (R15)

MS:437 (M+H)⁺, 381, 305
IR: 3340, 1675, 1602, 1540, 1488, 1232, 1165, 977cm⁻¹

B 16 (Method a) tert-Butyl (3R,4R)-3-(3,5-diethoxy-benzoylamino)-4-hydroxy-azepane-1-carboxylate as a colourless foam from tert-butyl (3R,4R)-4-benzyloxy-3-(3,5-diethoxy-benzoylamino)azepane-1-carboxylate (R16)
MS: 423.5 (M+H)⁺, 367.4, 323.4
IR: 3329, 1664, 1593, 1536, 1172, 1058 cm⁻¹

B 17 (Method a) tert-Butyl (3R,4R)-3-(3,5-diethyl-4-methoxy-methoxy-benzoylamino)-4-hydroxy-azepane-1-carboxylate as a colourless foam from tert-butyl (3R,4R)-benzyloxy-3-(3,5-diethyl-4-methoxymethoxy-benzoyl-amino)-azepane-1-carboxylate (R17)
MS: m/e=451.4 (M+H)⁺
IR (Flm): 3334, 1692, 1665, 1638, 1602, 1536, 1162, 1075 cm⁻¹

B18 (Method b) tert-Butyl (3R,4R)-4-hydroxy-3-(4-pyridinoyl-amino)-azepane-1-carboxylate as a yellow oil from tert-butyl (3R,4R)-3-amino-4-hydroxy-azepane-1-carboxylate
MS: 336.2(M+H)⁺;
IR: 3425, 1666, 1539, 1417, 1165, 847cm⁻¹

B 19 (Method a) tert-Butyl (3R,4R)-3-(3-tert-butyl-4-hydroxy-benzoylamino)-4-hydroxy-azepane-1-carboxylate as a colourless powder from tert-butyl (3R,4R)-4-benzyloxy-3-(3-tert-butyl-4-hydroxy-benzoylamino)azepane-1-carboxylate (R18)
MS: 405.3 (M–H)⁻
IR: 3294, 1668, 1599, 1545, 1419, 1269, 1168 cm⁻¹

B 20 (Method b) tert-Butyl (3R,4R)-3-(3-bromo-4-methoxymethoxy-benzoylamino)-4-hydroxy-azepane-1-carboxylate as a colourless foam from 3-bromo-4-methoxymethoxy-benzoic acid B 21 (Method a) tert-Butyl (3R,4R)-4-hydroxy-3-(3-isopropyl-4-methoxymethoxy-benzoylamino)-azepane-1-carboxylate as a colourless foam from tert-butyl (3R,4R)-4-benzyloxy-3-(3-isopropyl-4-methoxymethoxy-benzoylamino)azepane-1-carboxylate (R19)
MS: 437.4 (M+H)⁺, 381.4, 337.3
IR: 3333, 1665, 1637, 1604, 1539, 1492, 1243, 1162, 977 cm⁻¹

B 22 (Method a) tert-Butyl (3R,4R)-3-(3-sec-butyl-4-methoxy-methoxy-benzoylamino)-4-hydroxy-azepane-1-carboxylate as a colourless foam from tert-butyl (3R,4R)-4-benzyloxy-3-(3-sec-butyl-4-methoxymethoxy-benzoylamino)azepane-1-carboxylate (R20)
MS: 451.5 (M+H)⁺, 395.4, 351.3
IR: 3335, 1665, 1638, 1604, 1539, 1491, 1241, 1162, 1074, 998 cm⁻¹

B 23 (Method b) tert-Butyl (3R,4R)-3-(2-benzyloxy-5-fluoro-benzoylamino)-4-hydroxy-azepane-1-carboxylate as a light yellow foam from 2-benzyloxy-5-fluoro-benzoic acid acetone oxime ester
MS: 459.1 (M+H)⁺, 403.1,359.2
IR: 3389, 1686, 1657, 1532, 1488, 1417, 1274, 1187, 1003, 812, 744, 698 cm⁻¹

The starting material used in B 18 was prepared as follows:

Ethyl 2,3-dideoxy-α-D-erythrohexopyranoside was converted with p-toluenesulphochloride in pyridine in 6-O-(p-tolylsulphonyl)-2,3-dideoxy-α-D-erythrohexopyranoside reaction with sodium azide in dimethylformamide yielded ethyl 6-azido-2,3,6-trideoxy-alpha-D-erythrohexopyranoside from which with 4-nitrobenzoic acid under Mitsunobu reaction conditions there was obtained 6-azido-2,3,6-trideoxy-4-O-(4-nitrobenzoyl)-α-D-threohexopyranoside. Hydrolysis with methanolic NaOH yielded 6-azido-2,3,6-trideoxy-α-D-galactopyranoside from which by benzylation and subsequent acidic hydrolysis there was obtained 6-azido-5-O-benzyl-2,3,6-trideoxy-D-galactopyranose. Hydrogenation with PtO and reaction with bis-tert.-butyl carbonate yielded tert-butyl (3R,4R)-4-(benzyloxy)-hexahydro-3-hydroxy-1H-azepine-1-carboxylate. Under Mitsunobu conditions there was obtained therefrom tert.butyl (3S,4R)-4-benzyloxy)-hexahydro-3-O-(4-nitrobenzoyl)-1H-azepine-1-carboxylate and therefrom by basic hydrolysis and reaction with hydrazoic acid under Mitsunobu conditions there was obtained tert.-butyl (3R,4R)-3-azido-4-(benzyloxy)-hexahydro-1H-azepine-1-carboxylate. Hydrogenation of this compound over Pd/C at room temperature and atmospheric pressure yielded tert.butyl (3R,4R)-3-amino-4-benzyloxy-azepane-1-carboxylate, further hydrogenation at 80° C. and 10 bar yielded tert.-butyl (3R,4R)-3-amino-4-hydroxy-azepane-1-carboxylate as a colourless oil.

The starting material used in B 23 was prepared starting from 5-fluoro-2-hydroxy-benzoic acid by reaction with benzyl bromide in dimethylformamide to give benzyl 2-benzyloxy-5-fluoro-benzoate, basic hydrolysis and esterification with acetone oxime.

Example C

C. The acids used in Example A were prepared by:
method a) basic hydrolysis of corresponding esters; or
method b) oxidation of corresponding aldehydes with oxidizing agents such as sodium chlorite, peracids or KMnO4; or
c) oxidation of corresponding alcohols with oxidizing agents such as $MnO_2$.

The following compounds were obtained:

C 1 (Method a) 4-(2-Fluoro-4-methoxy-6-methoxymethoxy-benzoyl)-benzoic acid as colourless crystals, m.p. 136° C., from methyl 4-(2-fluoro-4-methoxy-6-methoxymethoxy-benzoyl)-benzoate (D4)

C 2 (Method a) 4-(2-Fluoro-6-methoxymethoxy-benzoyl)-benzoic acid as colourless crystals, m.p. 164° C., from methyl 4-(2-fluoro-6-methoxymethoxy-benzoyl)-benzoate (D5)

C 3 (Method a) 4-(2-Fluoro-3-methoxy-6-methoxymethoxy-benzoyl)-benzoic acid as colourless crystals, m.p. 167° C., from methyl 4-(2-fluoro-3-methoxy-6-methoxymethoxy-benzoyl)-benzoate (D6)

C 4 (Method b) 4-(3-m-Methoxymethoxy-naphthalen-2-ylcarbonyl)-benzoic acid from 4-(3-methoxymethoxy-naphthalen-2-ylcarbonyl)-benzaldehyde (L1)

C 5 (Method a) 4-(2,3-Difluoro-6-methoxymethoxy-benzoyl)-benzoic acid as colourless crystals, m.p. 181° C., from methyl 4-(2,3-difluoro-6-methoxymethoxy-benzoyl)-benzoate (D7)

C 6 (Method a) 4-(2,4-Difluoro-6-methoxymethoxy-benzoyl)-benzoic acid as colourless crystals, m.p. 139° C., from methyl 4-(2,4-difluoro-6-methoxymethoxy-benzoyl)-benzoate (D8)

C 7 (Method b) 4-(5-Methoxy-2-methoxymethoxy-benzoyl)-benzoic acid from 4-(5-methoxy-2-methoxymethoxy-benzoyl)-benzaldehyde (L2)

C 8 (Method b) 4-(3-Methoxymethoxy-5,6,7,8-tetrahydro-naphthalen-2-ylcarbonyl)-benzoic acid from 4-(3-methoxymethoxy-5,6,7,8-tetrahydro-naphthalen-2-ylcarbonyl)benzaldehyde (L3)

C 9 (Method a) 4-(2-Methoxymethoxy-5-dimethylamino-benzoyl)-benzoic acid as red crystals, m.p. 166° C., from methyl 4-(2-methoxy-methoxy-5-dimethylamino-benzoyl)-benzoate (D9)

C 10 (Method b) 4-(7-Methoxymethoxy-2,3-dihydro-1,4-benzodioxin-6-ylcarbonyl)benzoic acid from 4-(7-methoxymethoxy-2,3-dihydro-1,4-benzodioxin-6-ylcarbonyl)-benzaldehyde (L4))

C 11 (Method b) (RS)-4-[5-(1-Methoxyethyl)-2-methoxymethoxy-benzoyl]-benzoic acid from (RS)-4-[5-(1-methoxyethyl)-2-methoxy-methoxy-benzoyl]-benzaldehyde (L5)

C 12 (Method a) 4-(6-Methoxymethoxy-quinolin-7-ylcarbonyl)-benzoic acid from methyl 4-(6-methoxymethoxy-quinolin-7-ylcarbonyl)-benzoate ((D10)

C 13 (Method a) 4-(4-Methoxymethoxy-biphenyl-3-ylcarbonyl)-benzoic acid from methyl 4-(4-methoxymethoxy-biphenyl-3-ylcarbonyl)-benzoate (D11)

C 14 (Method b) 4-(5-Acetyl-2-methoxymethoxy-benzoyl)-benzoic acid from 4-(5-acetyl-2-methoxymethoxy-benzoyl)-benzaldehyde (L6)

C 15 (Method a) 4-(3-Methoxymethoxy-10-methyl-phenothiazin-2-ylcarbonyl)-benzoic acid as a yellow solid from methyl 4-(3-methoxymethoxy-10-methyl-phenothiazin-2-ylcarbonyl)-benzoate (D12)
M.p.=219° C. MS :422 (M)$^+$
IR: 3425, 1716, 1662, 1600, 1502, 1411, 1266, 1018.

C 16 (Method a) 4-(2-Methoxymethoxy-5-methyl-benzoyl)-benzoic acid as a white solid from methyl 4-(2-methoxymethoxy-5-methyl-benzoyl)-benzoate (D13)
M.p.: 128.2° C. MP: 300 (M)$^+$, 269, 238
IR: 3431, 1693, 1668, 1230, 1147, 1110, 998, 806.

C 17 (Method a) 4-(6-Methoxymethoxy),3-benzodioxol-5-yl-carbonyl)-benzoic acid from methyl 4-(6-methoxymethoxy-1,3-benzodioxol-5-ylcarbonyl)-benzoate (D14)

C 18 (Method a) 4-(5-Isopropyl-2-methoxymethoxy-benzoyl)-benzoic acid as a white solid from methyl 4-(5-isopropyl-2-methoxymethoxy-benzoyl)-benzoate (D15)
M.p.: 122° C. MS: 328 (M)$^+$, 297, 283
IR: 2963, 1693, 1661, 1605, 1495, 1292, 1002, 823.

C 19 (Method a) 4-(6-Methoxymethoxy-1,4-benzodioxin-5-yl-carbonyl)-benzoic acid as a yellow solid from methyl 4-(6-methoxymethoxy-1,4-benzodioxin-5-ylcarbonyl)benzoate (D16)
M.p.: 124.2° C. MS: 344 (M)$^+$, 299, 282
IR: 2937, 1677, 1599, 1483, 1270, 1073, 829.

C 20 (Method a) 4-(2-Fluoro-3-dimethylamino-6-methoxymethoxy-benzoyl)-benzoic acid as yellow crystals, m.p. 156° C., from methyl 4-(2-fluoro-3-dimethylamino-6-methoxymethoxy-benzoyl)-benzoate (D17)

C 21 (Method b) 4-(2-Fluoro-3-isopropyl-6-methoxymethoxy-benzoyl)-benzoic acid from 4-(2-fluoro-3-isopropyl-6-methoxy-methoxy-benzoyl)-benzaldehyde ((L6)

C 22 (Method a) 4-(2-Fluoro-6-methoxymethoxy-pyrrolidin-1-yl-benzoyl)-benzoic acid as orange crystals, m.p. 153° C., from methyl 4-(2-fluoro-6-methoxymethoxy-3-pyrrolidin-1-yl-benzoyl)-benzoate (D18)

C 23 (Method a) 4-(2-Fluoro-6-methoxymethoxy-3-methyl-benzoyl)-benzoic acid as a yellow solid from methyl 4-(2-fluoro-6-methoxymethoxy-3-methyl-benzoyl)-benzoate (D19)
M.p.: 148.5° C. MS: 318 (M)$^+$, 256
IR: 2827, 1699, 1675, 1487, 1263, 1055, 809.

C 24 (Method a) 4-(3-Ethyl-2-fluoro-6-methoxymethoxy-benzoyl)-benzoic acid as a light yellow solid from methyl 4-(3-ethyl-2-fluoro-6-methomethoxy-benzoyl)benzoate (D2)
M.p.: 148.5° C. MS: 332 (M)$^+$, 270
IR: 2934, 1703, 1679, 1468, 1265, 1150, 1036 809.

C 25 (Method a) 4-(2-Fluoro-6-methoxymethoxy-piperidin-1-yl-benzoyl)-benzoic acid as yellow crystals, m.p. 148° C., from 4-(2-fluoro-6-methoxymethoxy-3-piperidin-1-yl-benzoyl)-benzoate (D3)

C 26 (Method c) 3,5-Difluoro-4-(5-methoxy-2-methoxymethoxy-benzoyl)benzoic acid, m.p: 130–133 (AcOEt/hexane), from (RS)-3,5-difluoro-4-[hydroxy-(5-methoxy-2-methoxymethoxy-phenyl)-methyl]benzoic acid (prepared by nucleophilic addition of lithiated 3,5-difluorobenzoic acid to 5-methoxy-2-methoxy-methoxybenzaldehyde)

C 27 (Method a) 4-(2-Methoxymethoxy-5-methylthio-benzoyl)-benzoic acid as a yellow solid from methyl 4-(2-methoxymethoxy-5-methylthio-benzoyl)-benzoate (D20)
M.p: 129–130
MS: 332(M)$^+$, 302, 270, 45
IR: 2909, 1693, 1667, Example D D. The esters, aldehydes and alcohols used in Example C were prepared by:

method a) methoxymethylation of the compounds from Example (E) using chloromethyl methyl ether and NaH; or method b) oxidation of the compounds from Example (F) with $MnO_2$;

method c) nucleophilic addition of the compounds from Example (G) or corresponding known compounds to terephthalic acid 1-methyl ester 4-propan-2-one oxime ester; or method d) oxidation of the compounds of Example (F) with oxalyl chloride/DMSO.

The following compounds were prepared:

D 2 (Method c) Methyl 4-(3-ethyl-2-fluoro-6-methoxymethoxy-benzoyl)-benzoate as a colourless oil from 4-ethyl-2-fluoro-4-methoxymethoxy-benzene (G7) (nucleophile) and terephthalic acid 1-methyl ester 4-propan-2-one oxime ester (electrophile);
MS: 346 (M)$^+$, 315
IR: 2962, 1727, 1681, 1621, 1485, 1277, 1155, 1038, 816 cm$^{-1}$ D 3 (Method d) Methyl 4-(2-fluoro-6-methoxymethoxy-3-piperidin-1-yl-benzoyl)-benzoate as a yellow viscous oil from methyl (RS)-4-[(2-fluoro-6-methoxymethoxy-3-piperidin-1-yl-phenyl)-hydroxy-methyl]-benzoate
MS: m/e=401 (M)$^{+\cdot}$
IR (film): 1728, 1683, 1619, 1574, 1487, 1273 1038 cm$^{-1}$ D 4 (Method a) Methyl 4-(2-fluoro-4-methoxy-6-methoxymethoxy-benzoyl)-benzoate as light yellow crystals, m.p. 66° C., from methyl 4-(2-fluoro-6-hydroxy-4-methoxy-benzoyl)-benzoate (E3)

D 5 (Method a) Methyl 4-(2-fluoro-6-methoxymethoxy-benzoyl)-benzoate as colourless crystals, m.p. 75° C., from methyl 4-(2-fluoro-6-hydroxy-benzoyl)-benzoate (E2)

D 6 (Method b) Methyl 4-(2-fluoro-3-methoxy-6-methoxymethoxy-benzoyl)-benzoate as light yellow crystals from methyl (RS)-4-[(2-fluoro-3-methoxy-6-methoxymethoxy-phenyl)-hydroxy-methyl]-benzoate (F1)

D 7 (Method b) Methyl 4-(2,3-difluoro-6-methoxymethoxy-benzoyl)-benzoate as colourless crystals, m.p. 82° C., from methyl (RS)-4-[(2,3-difluoro-6-methoxymethoxy-phenyl)-hydroxy-methyl]-benzoate (F2)

D 8 (Method b) Methyl 4-(2,4-difluoro-6-methoxymethoxy-benzoyl)-benzoate as colourless crystals, m.p. 73° C., from methyl (RS)-4-[(2,4-difluoro-6-methoxymethoxy-phenyl)-hydroxy-methyl]-benzoate (F3)

D 9 (Method c) Methyl 4-(2-methoxymethoxy-5-dimethylamino-benzoyl)-benzoate from 1-dimethylamino-4-methoxymethoxy-benzene (G1)

D 10 (Method c) Methyl 4-(6-methoxymethoxy-quinolin-7-yl-carbonyl)-benzoate from 8-bromo-7-methoxymethoxy-quinoline (G2)

D 11 (Method b) Methyl 4-(4-methoxymethoxy-biphenyl-3-yl-carbonyl)-benzoate from methyl (RS)-4-[hydroxy-(4-methoxy-methoxy-biphenyl-3-yl)-methyl]-benzoate (F4)

D 12 (Method c) Methyl 4-(3-methoxymethoxy-10-methyl-phenothiazin-2-ylcarbonyl)-benzoate as an oil from 3-methoxymethoxy-10-methyl-phenothiazine (G3)
MS: 435 (M), 163
IR: 2948, 1713, 1651, 1600, 1500, 1329, 1138, 830, 734.

D 13 (Method c) Methyl 4-(2-methoxymethoxy-5-methyl-benzoyl)-benzoate as a white solid from 4-methoxymethoxy-toluene; m.p. 56° C.
MS: 314 (M), 283
IR: 2929, 1720, 1662, 1607, 1495, 1281, 991, 820 cm$^{-1}$.

D 14 (Method b) Methyl 4-(6-methoxymethoxy-1,3-benzodioxol-5-ylcarbonyl)-benzoate from methyl (RS)-4-[hydroxy-(6-methoxymethoxy-1,3-benzodioxol-5-yl)-methyl]-benzoate (F5)

D 15 (Method c) Methyl 4-(5-isopropyl-2-methoxymethoxy-benzoyl)-benzoate from 1-isopropyl-4-methoxymethoxy-benzene (G4)
MS: 342 (M), 311, 297
IR: 2959, 2825, 1725, 1662, 1606, 1497, 1279, 1237, 992, 820 cm$^{-1}$ D 16 (Method c) 4-(6-Methoxymethoxy-1,4-benzodioxin-5-ylcarbonyl)-benzoic acid as a yellow solid from 2,3-dihydroxy-6-(methoxymethoxy)-1,4-benzodioxin
MS: 358 (M), 327
IR: 2954, 1725, 1676, 1483, 1267, 800 cm$^{-1}$.

D 17 (Method c) Methyl 4-(2-fluoro-6-methoxymethoxy-3-dimethylamino-benzoyl)-benzoate from 1-fluoro-2-dimethylamino-4-methoxymethoxy-benzene (G5)

D 18 (Method d) Methyl 4-(2-fluoro-6-methoxymethoxy-3-pyrrolidin-1-yl-benzoyl)-benzoate as a yellow viscous oil from methyl (RS)-4-[(2-fluoro-6-methoxymethoxy-3-pyrrolidin-1-yl-phenyl)-hydroxy-methyl]-benzoate (F6)
MS: m/e=387 (M)$^{+\cdot}$
IR (flm): 1726, 1681, 1620, 1571, 1493, 1281 1041 cm$^{-1}$ D 19 (Method c) Methyl 4-(2-fluoro-6-methoxymethoxy-3-methyl-benzoyl)benzoate as a white solid from 2-fluoro-4-methoxymethoxy-toluene (G6)
MS: 332 (M), 301
IR: 2952, 1730, 1679, 1627, 1483, 1279, 1155, 1024, 819 cm$^{-1}$.

D 20 (Method d) Methyl 4-(2-methoxymethoxy-5-methylthio-benzoyl)-benzoate as a yellow oil from methyl (RS)-4-[hydroxy-(2-methoxymethoxy-5-methylthio-phenyl)-methyl]benzoate ((F8)
MS: 346(M)$^+$, 316, 270, 45
IR: 3433, 1734, 1724, 1664, 1485, 1284, 1237, 985 814 cm$^{-1}$ D 21 (Method b) Methyl 4-(2-fluoro-4,6-dimethoxy-benzoyl)-benzoate as colourless crystals, m.p. 99° C., from methyl (RS)-4-[(2-fluoro-4,6-dimethoxy-phenyl)-hydroxy-methyl]-benzoate (F10)

Example E

The compounds of Examples D1 and D21 were reacted further as follows:

E 1 11 ml of boron tribromide were added dropwise at −78° C. to a solution of 28.83 g of methyl 4-(5-fluoro-2-methoxy-benzoyl)-benzoic in 250 ml of dichloromethane. The reaction mixture was stirred at −78° C. under argon for one hour. After the addition of 100 ml of methanol the solvent was removed as far as possible. After again adding 100 ml of ice-cold methanol the separated product was filtered off under suction, washed with 50 ml of ice-cold methanol, suction dried as far as possible and recrystallized from ethyl acetate/hexane. There were obtained 26 g of methyl 4-( 2-fluoro-6-hydroxy-benzoyl)-benzoate as yellow crystals. M.p. 101° C.

In an analogous manner there were prepared:

E 2 Methyl 4-(2-fluoro-6-hydroxy-4-methoxy-benzoyl)-benzoate as colourless crystals, m.p. 154° C, from methyl 4-(2-fluoro-4,6-dimethoxy-benzoyl)-benzoate (D21)

Example F

F. The starting materials for Examples D3, D6, D7, D8, D11, D14, D18, D20, D21 and D22 were prepared by nucleophilic addition of compounds of Example (G) to methyl 4-formylbenzoate:

F 1 Methyl (RS)-4-[(2-fluoro-3-methoxy-6-methoxymethoxy-phenyl)-hydroxy-methyl]-benzoate, colourless crystals, m.p. 66° C., from 1-fluoro-2-methoxy-5-methoxymethoxy-benzene (G8)

F 2 Methyl (RS)-4-[(2,3-difluoro-6-methoxymethoxy-phenyl)-hydroxy-methyl]-benzoate from 1,2-difluoro-4-methoxymethoxy-benzene (G9)

F 3 Methyl (RS)-4-[(2,4-difluoro-6-methoxymethoxy-phenyl)-hydroxy-methyl]-benzoate from 1,3-difluoro-5-methoxymethoxy-benzene (G10)

F 4 Methyl (RS)-4-[hydroxy-(4-methoxymethoxy-biphenyl-3-yl)methyl]-benzoate from 4-methoxymethoxy-biphenyl F 5 Methyl (RS)-4-[hydroxy-(6-methoxymethoxy-1,3-benzodioxol-5-yl)-methyl]-benzoate from 5-bromo-6-methoxymethoxy-1,3-benzodioxol F 6 Methyl (RS)-4-[(2-fluoro-6-methoxymethoxy-3-pyrrolidin-1-yl-phenyl)-hydroxy-methyl]-benzoate from 1-(2-fluoro-4-methoxymethoxy-phenyl)-pyrrolidine (G11)

F 7 Methyl (RS)-4-[(2-fluoro-6-methoxymethoxy-3-piperidin-1-yl-phenyl)-hydroxy-methyl]-benzoate from 1-(2-fluoro-4-methoxymethoxy-phenyl)-piperidine ((G12)

F 8 Methyl (RS)-4-[hydroxy-(2-methoxymethoxy-5-methylthio-phenyl)-methyl]-benzoate as a yellow oil from 1-methoxymethoxy-4-methylthiobenzene
MS: 348 (M)$^+$, 286, 271, 227, 45
IR: 3456, 1721, 1484, 1282, 1110, 995, 815 cm$^{-1}$ F 9 Methyl (RS)-4-[(2-fluoro-6-methoxy-phenyl)-hydroxy-methyl]-benzoate as colourless crystals, m.p. 115° C., from 3-fluoro-anisole F 10 Methyl (RS)-4-[(2-fluoro-4,6-dimethoxy-phenyl)-hydroxy-methyl]-benzoate from 5-fluoro-1,3-dimethoxybenzene.

Example G

G. The starting materials for Examples D2, D9, D10, D12, D15, D17, D19, F1, F2, F3, F6 and F7 were prepared by O-alkylation of the corresponding phenols:

G 1 1-Dimethylamino-4-methoxymethoxy-benzene as a light yellow oil from 4-hydroxy-N,N-dimethylaniline
B.p. 100° C./0.2 mbar
MS: m/e=181 (M)$^{+\cdot}$, 136
IR (film): 1615, 1515, 1235, 1201, 1151, 1077, 1017 cm$^{-1}$ G 2 8-Bromo-7-methoxymethoxy-quinoline from 7-bromo-quinolin-6-ol G 3 3-Methoxymethoxy-10-methyl-phenothiazine as an oil from 10-methyl-phenothiazin-3-ol G4 1-lsopropyl-4-methoxymethoxy-benzene as colourless oil from 4-isopropyl-phenol
MS: 180 (M), 165, 135
IR: 2960, 1610, 1512, 1234, 1009, 831.

G 5 1-Fluoro-2-dimethylamino-5-methoxymethoxy-benzene as a colourless oil from 3-fluoro-4-dimethylamino-phenol (H3)
MS: m/e=199 (M)$^{+\cdot}$, 154, 45
IR (KBr): 1575, 1512, 1273, 1250, 1150, 1011 cm$^{-1}$ G 6 2-Fluoro-4-methoxymethoxy-toluene as an oil from 3-fluoro-4-methyl-phenol (H2).
MS: 170 (M)
IR: 2956, 1630, 1590, 1510, 1265, 1153, 1012, 850
Anal. calc. for $C_9H_{11}O_2F$ (170.183): C 63.52, H 6.52; found: C 63.25, H 6.52.

G 7 1-Ethyl-2-fluoro-4-methoxymethoxy-benzene as an oil from 4-ethyl-3-fluoro-phenol (H1).

G 8 1-Fluoro-2-methoxy-5-methoxymethoxy-benzene as a colourless oil from 3-fluoro-4-methoxyphenol
B.p. 165° C./10 mbar
MS: m/e=186 (M)$^{+\cdot}$, 45
IR (film): 1599, 1512, 1266, 1223, 1153, 1121, 1077, 1030, 1009 cm$^{-1}$ G 9 1,2-Difluoro-4-methoxymethoxy-benzene as a colourless oil, b.p. 86° C./10 mbar, from 3,4-difluorophenol
MS: m/e=174 (M)$^{+\cdot}$, 45
IR (film): 1616, 1516, 1256, 1220, 1204, 1153, 1077, 1007 cm$^{-1}$ G 10 1,3-Difluoro-5-methoxymethoxy-benzene as a colourless oil from 3,5-difluorophenol
B.p. 79° C./10 mbar
MS: m/e=174 (M)$^{+\cdot}$, 45
IR (film): 1628, 1600, 1472, 1224, 1156, 1138, 1116, 1080, 1028 cm$^{-1}$ G 11 1-(2-Fluoro-4-methoxymethoxy-phenyl)-pyrrolidine as a light yellow oil from 3-fluoro-4-(pyrrolidin-1-yl)-phenol (H4)
B.p. 135° C./0.2 mbar
MS: m/e=225 (M)$^{+\cdot}$, 180
IR (film): 1579, 1516, 1270, 1152, 1015 cm$^{-1}$ G 12 1-(2-Fluoro-4-methoxymethoxy-phenyl)-piperidine as a colourless oil from 3-fluoro-4-(piperidin-1-yl)-phenol (H2)
B.p. 135° C./0.2 mbar
MS: m/e=239 (M)$^{+\cdot}$, 194, 45
IR (film): 1628, 1582, 1508, 1272, 1257, 1154, 1012 cm$^{-1}$ Example H H. The starting materials for Examples G5, G7, G11, and G12 were prepared by O-dealkylation of corresponding precursors,
method a) with phosphorus tribromide, or
method b) HBr/glacial acetic acid as follows:

H 1 (Method a) 4-Ethyl-3-fluoro-phenol as a liquid from 1-ethyl-2-fluoro-4-methoxy-benzene (I1)
MS: 141, 125
IR: 3343, 2971, 1626, 1598, 1509, 1283, 1148, 844 cm$^{-1}$.

H 2 (Method b) 3-Fluoro-4-(piperidin-1-yl)-phenol as a colourless solid from 1-(2-fluoro-4-methoxy-phenyl)-piperidine (I3); m.p. 134° C.

H 3 (Method b) 3-Fluoro-4-dimethylamino-phenol as a grey-white solid from 1-fluoro-2-dimethylamino-5-methoxy-benzene (I2)

H 4 (Method b) 1-(2-Fluoro-4-hydroxy-phenyl)-pyrrolidine as a grey-white solid from 1-(2-fluoro-4-methoxy-phenyl)-pyrrolidine Example I I. The starting materials for Examples H were prepared by reduction of,
method a) a corresponding acetophenone; or
method b) a corresponding amide as follows:

I 1 (Method a) 1-Ethyl-2-fluoro-4-methoxy-benzene as a yellow liquid from 2-fluoro-4-methoxy-acetophenone
MS: 154 (M), 139 (M—CH$_3$)
IR: 2400, 1627, 1585, 1285, 1154, 1034, 833 cm$^{-1\cdot}$ I 2 (Method b) 1-Fluoro-2-dimethylamino-5-methoxy-benzene as colourless crystals from N-(2-fluoro-4-methoxy-phenyl)-N-methyl-formamide (J1)
M.p.: 125–126° C.

I 3 (Method b) 1-(2-Fluoro-4-methoxy-phenyl)-piperidine as a light yellow oil (b.p. 125° C./0.2 mbar) from 1-(2-fluoro-4-methoxy-phenyl)-piperidin-2-one (J2)
MS: m/e=209 (M)$^{+\cdot}$, 208 (M—H)$^+$, 194
IR (KBr): 1626, 1580, 1510, 1230, 1157, 1140, 1120, 1043 cm$^{-1}$ I 4 (Method b) 1-(2-Fluoro-4-methoxy-phenyl)-pyrrolidine as colourless crystals, m.p.143° C, from 1-(2-fluoro-4-methoxy-phenyl)-pyrrolidin-2-one (J3)

Example J

J. The starting materials for Examples I 2, I 3 and I 4 were prepared by:
method a) methylation of a corresponding N-formanilide, or
method b) basic cyclization of a corresponding N-bromanilide as follows:

J 1 (Method a) N-(2-Fluoro-4-methoxy-phenyl)-N-methyl-formamide as a colourless viscous oil from N-(2-fluoro-4-methoxy-phenyl)-formamide (K1 )
MS: m/e=183 (M)$^{+\cdot}$, 140
IR (film): 1683, 1624, 1587, 1516, 1289, 1160 cm$^{-1}$ J 2 (Method b) 1-(2-Fluoro-4-methoxy-phenyl)-piperidin-2-one as colourless crystals, m.p.: 92° C., from 5-bromo-N-(2-fluoro-4-methoxy-phenyl)-valeramide (K2)

J 3 (Method b) 1-(2-Fluoro-4-methoxy-phenyl)-pyrrolidin-2-one as a light yellow viscous oil from 4-bromo-N-(2-fluoro-4-methoxy-phenyl)-butyramide (K3)
MS: m/e=209 (M)$^{+\cdot}$, 154
IR (film): 1700, 1624, 1588, 1516, 1287, 1158 cm$^{-1}$ Example K K. The starting materials for Examples J were prepared by,
method a) formylating a corresponding aniline; or
method b) acylating a corresponding aniline:

K 1 (Method a) N-(2-Fluoro-4-methoxy-phenyl)-formamide, colourless crystals, from 2-fluoro-4-methoxyaniline
MS: m/e=169 (M)$^{+\cdot}$, 126
IR (KBr): 1658, 1646, 1621, 1590, 1525, 1460, 1429, 1390, 1300, 1223, 1180, 1110, 1035, 872, 802 cm$^{-1}$ K 2 (Method b) 5-Bromo-N-(2-fluoro-4-methoxy-phenyl)-valeramide, colourless crystals, m.p. 99° C., from 2-fluoro-4-methoxyaniline and 5-bromovaleric acid K 3 (Method b) 4-Bromo-N-(2-fluoro-4-methoxy-phenyl)-butyramide, colourless crystals, m.p. 88° C., from 2-fluoro-4-methoxyaniline and 4-bromobutyric acid Example L L. The aldehydes used in Example B, method b), were prepared as follows according to the process of Example D:

L 1 4-(3-Methoxymethoxy-naphthalen-2-ylcarbonyl) benzaldehyde (from (4-hydroxymethyl-phenyl)-(3-methoxymethoxy-naphthalen-2-yl)-methanone (M1)

L 2 4-(5-Methoxy-2-methoxymethoxy-benzoyl)-benzaldehyde from (RS)-(4-hydroxymethyl-phenyl)-(5-methoxy-2-methoxymethoxy-phenyl)-methanol (M2)

L 3 4-(3-Methoxymethoxy-5,6,7,8-tetrahydro-naphthalen-2-yl-carbonyl)benzaldehyde from (RS)-(4-hydroxymethyl-phenyl)-(3-methoxymethoxy-5,6,7,8-tetrahydro-naphthalen-2-yl)-methanol (M3)

L 4 4-(7-Methoxymethoxy-2,3-dihydro-1,4-benzodioxin-6-ylcarbonyl)-benzaldehyde from (RS)-(4-hydroxymethyl-phenyl)-(7-methoxymethoxy-2,3-dihydro-1,4-benzodioxin-6-yl)methanol (M4)

L 5 (RS)-4-[5-(1-Methoxyethyl)-2-methoxymethoxy-benzoyl]-benzaldehyde from (SR)-(4-hydroxymethyl-phenyl)-[5-[(RS) and (SR)-1-methoxyethyl]-2-methoxymethoxyphenyl]-methanol (M5)

L 6 4-(5-Acetyl-2-methoxymethoxy-benzoyl)-benzaldehyde (from (RS)-1-[3-[(RS) and (SR)-hydroxy-(4-hydroxymethyl-phenyl)-methyl]-4-methoxymethoxyphenyl]-ethanol (M6)

L 7 4-(2-Fluoro-3-isopropyl-6-methoxymethoxy-benzoyl)-benzaldehyde from (RS)-(2-fluoro-3-isopropyl-6-methoxymethoxy-phenyl)-(4-hydroxymethyl-phenyl)-methanol (M7)

M

M. The compounds used in Example L were prepared by,
method a) O-desilylation of compounds of Example N; or
method b) nucleophilic addition of the Li salt of 4-bromobenzyl alcohol to the compounds of Example O or corresponding known compounds; or
method c) oxidation of compounds of Example N and subsequent O-desilylation.

M 1 (Method a) (4-Hydroxymethyl-phenyl)-(3-methoxymethoxy-naphthalen-2-yl)-methanone from [4-(tert-butyl-dimethyl-silanyloxymethyl)-phenyl]-(3-methoxymethoxy-naphthalen-2-yl)-methanone (N1)

M 2 (Method b) (RS)-(4-Hydroxymethyl-phenyl)-(5-methoxy-2-methoxymethoxy-phenyl)-methanol from 5-methoxy-2-methoxymethoxy-benzaldehyde.

M 3 (Method a) (RS)-(4-Hydroxymethyl-phenyl)-(3-methoxymethoxy-5,6,7,8-tetrahydro-naphthalen-2-yl)-methanol from (RS)-[4-(tert-butyl-dimethyl-silanyloxymethyl)-phenyl]-(3-methoxymethoxy-5,6,7,8-tetrahydro-naphthalen-2-yl)-methanol (N2)

M 4 (Method b) (RS)-(4-Hydroxymethyl-phenyl)-(7-methoxymethoxy-2,3-dihydro-1,4-benzodioxin-6-yl) methanol from 7-methoxymethoxy-2,3-dihydro-1,4-benzodioxin-6-carbaldehyde (O1)

M 5 (Method b) (SR)-(4-Hydroxymethyl-phenyl)-[5-[(RS) and (SR)-1-methoxyethyl]-2-methoxymethoxyphenyl]-methanol from (RS)-5-(1-methoxyethyl)-2-methoxymethoxy-benzaldehyde (O2)

M 6 (Method a) (RS)-1-[3-[(RS) and (SR)-Hydroxy-(4-hydroxymethyl-phenyl)-methyl]-4-methoxymethoxyphenyl]-ethanol from (RS)-[5-[(RS) and (SR)-1-(tert-butyldimethylsilanyloxy)-ethyl]-2-methoxymethoxyphenyl]-(4-hydroxymethyl-phenyl)-methanol (N3)

M 7 (Method a) (RS)-(2-Fluoro-3-isopropyl-6-methoxymethoxy-phenyl)-(4-hydroxymethyl)-phenyl-methanol from (RS)-[4-(tert-butyldimethylsilanyloxymethyl)-phenyl]-(2-fluoro-3-isopropyl-6-methoxymethoxy-phenyl)-methanol (N4)

M 8 (Method c) (4-Hydroxymethyl-phenyl)-(5-methoxy-2-methoxymethoxy-phenyl)-methanone from (RS)-[4-(tert-butyl-dimethylsilanyloxy-methyl)-phenyl]-(5-methoxy-2-methoxymethoxy-phenyl)-methanol (N5)

Example N

N. The compounds used in Example M in methods a) and c) were prepared by,
method a) nucleophilic addition of lithiated [(4-bromobenzyl)oxy]tert-butyldimethylsilane to methyl 3-ethoxymethoxy-naphthalene-2-carboxylate; or
method b) nucleophilic addition of the Li reagent used in a) to compounds of Example O or corresponding known compounds; or
method c) nucleophilic addition of lithiated 4-bromobenzyl alcohol to compounds of Example O; or
method d) nucleophilic addition of compounds of Example 53 to (4-formylbenzyl)oxy]tert-butyldimethylsilane The following compounds were thus-prepared:

N 1 (Method a) [4-(tert-Butyl-dimethyl-silanyloxymethyl)-phenyl]-(3-methoxymethoxy-naphthalen-2-yl)-methanone from [(4-bromobenzyl)oxy]tert-butyldimethylsilane and methyl 3-methoxymethoxy-naphthalene-2-carboxylate.

N 2 (Method b) (RS)-[4-(tert-Butyldimethylsilanyloxymethyl)-phenyl]-(3-methoxymethoxy-5,6,7,8-tetrahydro-naphthalen-2-yl)-methanol from 3-methoxymethoxy-5,6,7,8-tetrahydro-naphthalene-2-carbaldehyde (O3)

N 3 (Method c) (RS)-[5-[(RS) and (SR)-1-(tert-Butyldimethyl-silanyloxy)-ethyl]-2-methoxymethoxyphenyl]-(4-hydroxymethyl-phenyl)-methanol from (RS)-5-[(1-tertbutyldimethylsilanyl-oxy)ethyl]-2-methoxymethoxy-benzaldehyde (O4)

N 4 (Method d) (RS)-[4-(tert-Butyldimethylsilanyloxymethyl)-phenyl]-(2-fluoro-3-isopropyl-6-methoxymethoxy-phenyl)-methanol from 2-fluoro-4-methoxymethoxy-1-(1-methylethyl)benzene and (4-formylbenzyl)oxy]tert-butyldimethylsilane N 5 (Method b) (RS)-[4-(tert-Butyldimethylsilanyloxymethyl)-phenyl]-(5-methoxy-2-methoxymethoxy-phenyl)-methanol from 5-methoxy-2-methoxymethoxy-benzaldehyde Example O O. The compounds used in Example M and N were prepared by
method a) methoxymethylating known phenols; or
method b) oxidizing compounds [of] Example P The following compounds were thus-prepared:

O 1 (Method a) 7-Methoxymethoxy-2,3-dihydro-1,4-benzodioxin-6-carbaldehyde from 7-hydroxy-2,3-dihydro-1,4-benzodioxin-6-carbaldehyde O 2 (Method b) 5-(1-Methoxyethyl)-2-methoxymethoxy-benzaldehyde from (RS)-[5-(1-methoxyethyl)-2-methoxymethoxy-phenyl]-methanol ((P1)

O 3 (Method a) 3-Methoxymethoxy-5,6,7,8-tetrahydro-naphthalene-2-carbaldehyde from 3-hydroxy-5,6,7,8-tetrahydro-naphthalene-2-carbaldehyde O 4 (Method b) (RS)-5-[(1-tert Butyldimethylsilanyloxy)ethyl]-2-methoxymethoxy-benzaldehyde from (RS)-5-[(1-tert butyldimethyl-silanyloxy)-ethyl]-2-methoxymethoxy-phenyl]methanol (P2)

The starting materials used in N 4 were prepared as follows:

a) 2-Fluoro-4-hydroxy-acetophenone was converted with chloromethyl methyl ether in the presence of NaH into 2-fluoro-4-methoxymethoxy-acetophenone which with methyltriphenyl-phosphonium bromide in a Wittig reaction yielded 2-fluoro-4-methoxymethoxy-1-(1-methylvinyl)benzene. Hydrogenation over Pd/C yielded 2-fluoro-4-methoxymethoxy-1-(1-methylethyl)-benzene.

b) [4-(Formylbenzyl)oxy]tert.-butyldimethylsilane was obtained by formylating [(4-bromobenzyl)oxy]tert.-butyldimethylsilane with BuLi/dimethylformamide at −78° C.

Example P

P. The compounds used in Examples O2 and O4 were prepared by the reduction of compounds of Example Q:

P 1 (RS)-[5-(1-Methoxyethyl)-2-methoxymethoxy-phenyl]-methanol from methyl (RS)-5-(1-methoxyethyl)-2-methoxymethoxy-benzoate (Q2)

P 2 (RS)-5-[(1-tert Butyldimethylsilanyloxy)-ethyl]-2-methoxymethoxy-phenyl]methanol from methyl (RS)-5-[(1-tert-butyl-dimethyl-silanyloxy)-ethyl]-2-methoxymethoxy-benzoate (Q1)

Example Q

Q The compounds P1 and P2 were prepared as follows:

Methyl 5-acetyl-2-hydroxybenzoate was converted into methyl 5-acetyl-2-methoxymethoxy-benzoate from which by reduction with sodium borohydride there was obtained methyl (RS)-5-(1-hydroxyethyl)-2-methoxymethoxy-benzoate. Therefrom by O-silylation there was obtained:

Q 1 methyl (RS)-5-[(1-tert-butyl-dimethyl-silanyloxy)-ethyl]-2-methoxymethoxy-benzoate and by O-alkylation there was obtained Q 2 methyl (RS)-5-(1-methoxyethyl)-2-methoxymethoxy-benzoate Example R R. The compounds used in Example B were prepared by the acylation of tert-butyl (3R,4R)-4-benzyloxy-azepane-1-carboxylate (S) with known carboxylic acids or activated carboxylic acids prepared in a manner known per se.

The following compounds were thus-prepared:

R 1 tert-Butyl (3R,4R)-4-benzyloxy-3-(4-methoxymethoxy-benzoylamino)-azepane-1-carboxylate from 4-(methoxymethoxy)-benzoic acid;

R 2 tert-Butyl (3R,4R)-4-benzyloxy-3-[4-[dimethyl-(1,1,2-trimethylpropyl)siloxy]-benzoylamino]azepane-1-carboxylate as a colourless oil from 4-[dimethyl(1,1,2-trimethylpropyl)siloxy]-benzoic acid
IMS: 583 (M+H)$^+$, 527, 483, 263
IR: 3343, 1693, 1663, 1605, 1534, 1491, 1416, 1243, 1165, 1148, 1072, 996, 737, 698 cm$^{-1}$ R 3 tert-Butyl (3R,4R)-4-benzyloxy-3-(3-methoxy-4-methoxymethoxy-benzoylamino)-azepane-1-carboxylate as a colourless viscous oil from 3-methoxy-4-methoxymethoxybenzoic acid R 4 tert-Butyl (3R,4R)-4-benzyloxy-3-(5-methoxy-2-methoxy-methoxy-benzoylamino)-azepane-1-carboxylate from 5-methoxy-2-methoxymethoxy-benzoic acid R 5 tert-Butyl (3R,4R)-4-benzyloxy-3-[4-(tert-butyl-dimethyl-silanyloxy)-benzoylamino]-azepane-1-carboxylate from 4-(tert-butyldimethylsilanyloxy)benzoic acid R 6 tert-Butyl (3R,4R)-4-benzyloxy-3-(3,5-dimethoxy-4-methoxymethoxy-benzoylamino)-azepane-1-carboxylate as a colourless foam from 3,5-dimethoxy-4-methoxymethoxybenzoic acid
MS: 545.4 (M+H)$^+$
IR (film): 3326, 1693, 1663, 1585, 1539, 1159, 1079 cm$^{-1}$ R 7 tert-Butyl (3R,4R)-4-benzyloxy-3-(3,5-bis-methoxymethoxy-naphthalen-2-ylcarbonylamino)-azepane-1-carboxylate from 3,5-bis(methoxymethoxy)-2-naphthoic acid R 8 tert-Butyl (3R,4R)-4-benzyloxy-3-(3,5-dimethyl-benzoyl-amino)azepane-1-carboxylate as a colourless oil from 3,5-dimethoxybenzoic acid
MS: 513.7 (M+H)$^+$, 457.6, 413.5
IR: 3330, 1694, 1665, 1593, 1531, 1416, 1172, 1059, 764, 699 cm$^{-1}$ R 9 tert-Butyl (3R,4R)-4-benzyloxy-3-(3-methoxy-2-methoxy-methoxy-benzoyl-amino)-azepane-1-carboxylate as a colourless viscous oil from 3-methoxy-2-(methoxymethoxy) benzoic acid
MS: 515.5 (M+H)$^+$
IR (film): 3378, 1690, 1658, 1579, 1523, 1166, 1077 cm$^{-1}$ R 10 tert-Butyl (3R,4R)-4-benzyloxy-3-(3-methoxymethoxy-naphthalen-2-ylcarbonylamino)-azepane-1-carboxylate (Ro 48–4163) from 3-methoxymethoxy-2-naphthalene-2-carboxylic acid R 11 tert-Butyl (3R,4R)-4-benzyloxy-3-(4-methoxymethoxy-2,3,6-trimethyl-benzoyl-amino)-azepane-1-carboxylate as a colourless foam from 4-methoxymethoxy-2,3,6-trimethyl-benzoic acid
MS: 527.6 (M+H)$^+$
IR (KBr): 3326, 1694, 1638, 1597, 1524, 1156, 1065 cm$^{-1}$ R 12 tert-Butyl (3R,4R)-4-benzyloxy-3-(3,5-diisopropyl-4-methoxymethoxy-benzoyl-amino)-azepane-1-carboxylate as a colourless foam from 4-methoxymethoxy-3,5-bis-(1-methyl-ethyl)benzoic acid
MS: 569.9 (M+H)$^+$
IR (film): 3330, 1695, 1664, 1603, 1531, 1162, 1070 cm$^{-1}$ R 13 tert-Butyl (3R,4R)-4-benzyloxy-3-(3,4,5-trimethoxy-benzoyl-amino)azepane-1-carboxylate as a colourless powder from 3,4,5-trimethoxybenzoic acid
MS: 519.4 (M+H)$^+$441.4, 397.
IR: 3273, 1696, 1664, 1632, 1584, 1542, 1416, 1234, 1128, 736, 697 cm$^{-1}$ R 14 tert-Butyl (3R,4R)-benzyloxy-3-(4-methoxymethoxy-3,5-dimethyl-benzoylamino)-azepane-1-carboxylate as a colourless foam from 4-methoxymethoxy-3,5-dimethylbenzoic acid
MS: 511.8 (M+H)$^+$
IR (film): 3342, 1693, 1665, 1602, 1530, 1161, 1072 cm$^{-1}$ R 15 tert-Butyl (3R,4R)-3-(3-acetyl-4-methoxymethoxy-benzoyl-amino)-4-benzyloxy-azepane-1-carboxylate as a colourless foam from 3-acetyl-4-methoxymethoxybenzoic acid
MS: 527.5 (M+H)$^+$, 471.6
IR: 3334, 1680, 1663, 1603, 1535, 1487, 1415, 1165, 1086, 977, 738, 698 cm$^{-1}$ R 16 tert-Butyl (3R,4R)-4-benzyloxy-3-(3,5-diethoxy-benzoyl-amino)azepane-1-carboxylate, light yellow oil, from 3,5-diethoxy-benzoic acid MS: 485.7 (M+H)⁺, 429.5, 385.6
IR: 3334, 1737, 1665, 1595, 1532, 1419, 1363, 1158, 1066, 765, 700 cm⁻¹

R 17 tert-Butyl (3R,4R)-benzyloxy-3-(3,5-diethyl-4-methoxy-methoxy-benzoyl-amino)-azepane-1-carboxylate, colourless foam, from 3,5-diethyl-4-methoxymethoxy benzoic acid
MS: 541.5 (M+H)⁺
IR (film): 3335, 1694, 1665, 1604, 1532, 1162, 1074 cm⁻¹

R 18 tert-Butyl (3R,4R)-4-benzyloxy-3-(3-tert-butyl-4-hydroxy-benzoylamino)azepane-1-carboxylate, colourless powder, from 3-(1,1-dimethylethyl)-4-hydroxy-benzoic acid
MS: 513.4 (M−H)⁻
IR: 3324, 1665, 1637, 1601, 1551, 1417, 1272, 1156, 735, 697 cm⁻¹

R 19 tert-Butyl (3R,4R)-4-benzyloxy-3-(3-isopropyl-4-methoxymethoxy-benzoylamino)azepane-1-carboxylate, colourless oil, from 4-methoxymethoxy-2-(1-methylethyl)benzoic acid
MS: 527.5 (M+H)⁺, 471.5, 427.4
IR: 3346, 2960, 1695, 1665, 1604, 1537, 1500, 1259, 1165, 1100, 909 cm⁻¹

R 20 tert-Butyl (3R,4R)-4-benzyloxy-3-(3-sec-butyl-4-methoxy-methoxy-benzoylamino)azepane-1-carboxylate, colourless oil, from 4-methoxymethoxy-2-(1-methylpropyl)benzoic acid
MS: 541.5 (M+H)⁺, 485.5, 441.5
IR: 3341, 1694, 1663, 1605, 1534, 1491, 1416, 1241, 1165, 1150, 1074, 996, 736, 698 cm¹

Example S

S. The tert-butyl (3R,4R)-3-amino-4-benzyloxy-azepane-1-carboxylate used in Example (R) was prepared as follows:
Ethyl 2,3,6-trideoxy-alpha-D-erythrohexopyranoside was converted with p-toluenesulphochloride into ethyl 6-O-(p-tolylsulphonyl)-2,3-dideoxy-alpha-D-erythrohexopyranoside. By reaction with sodium azide there was obtained therefrom ethyl 6-azido-2,3,6-trideoxy-α-D-erythrohexopyranoside and therefrom with 4-nitrobenzoic acid under Mitsunobu conditions there was obtained ethyl 6-azido-2,3,6-trideoxy-4-0(4-nitrobenzoyl)-alpha-D-threohexopyranoside. Basic hydrolysis of the latter compound yielded ethyl 6-azido-2,3,6-trideoxy-α-D-galactopyranoside which by benzylation and subsequent acidic hydrolysis was converted into 6-azido-5-O-bnzyl-2,3,6-trideoxy-D-galactopyranose. Catalytic hydrogenation (PtO/room temperature) and subsequent reaction with bis-tert-butyl carbonate yielded tert butyl (3S,4R)-4 (benzyloxy)-hexahydro-3-hydroxy-1H-azepine-1-carboxylate. Acylation under Mitsunobu conditions to tert butyl (3S,4R)-4-(benzyloxy)-hexahydro-3-O-(4-nitrobenzoyl)-1H-azepine-i-carboxylate, basic hydrolysis and reaction with hydrazoic acid under Mitsunobu conditions yielded tert-butyl (3R,4R)-3-azido-4-(benzyloxy)-hexahydro-1H-azepine-1-carboxylate, from which the amine used in Example S was obtained by hydrogenation (Pd/C).

Example T

T. The compounds used in Examples 65–67 were prepared from compounds of Example A by
method a) hydrogenation of a benzyl group; or
method b) desilylation.
In this manner there were prepared:

T 1 (Method a) tert-Butyl (3R,4R)-3-(5-fluoro-2-hydroxy-benzoylamino)-4-[4-(5-methoxy-2-methoxymethoxy-benzoyl)-benzoyloxy]-azepine-1-carboxylate, colourless foam, from tert-butyl (3R,4R)-3-(2-benzyloxy-5-fluoro-benzoylamino)-4-[4-(5-methoxy-2-methoxymethoxy-benzoyl)-benzoyloxy]-azepine-1-carboxylate (the latter compound prepared from (B23) and (C7);

T 2 (Method b) tert-Butyl (3R,4R)-4-[3,5-difluoro-4-(5-methoxy-2-methoxymethoxy-benzoyl)-benzoyloxy]-3-(4-hydroxy-benzoylamino)-azepane-1-carboxylate (Ro 47–2629), light yellow foam, from tert-butyl (3R,4R)-4-[(3,5-difluoro-4-(5-methoxy-2-methoxymethoxy-benzoyl)benzoyloxy]-3-(4-[dimethyl-(1,1,2-trimethylpropyl)-silanyloxy]-benzoylamino]-4-hydroxy-azepane-1-carboxylate (A1)

T 3 (Method b) tert-Butyl (3R,4R)-3-(4-hydroxy-benzoylamino)-4-[4-(2-methoxymethoxy-5-methylthio-benzoyl)-benzoyloxy)-azepane-1-carboxylate, yellow foam, from tert-butyl (3R,4R)-4-[4-(2-methoxymethoxy-5-methylthio-benzoyl)-benzoyloxy]-3-[4-[dimethyl(1,1,2-trimethylpropyl)siloxy]-benzoylamino)-azepane-1-carboxylate
MS: 665.4 (M+H)⁺, 609.4
IR: 3391, 1720, 1666, 1609, 1505, 1277, 1158, 1105, 983, 848 cm⁻¹

Example U

U. The compounds used in Examples 68–76 were prepared by reduction of an azide to the amine and acylation with known activated benzoic acid derivatives. In this manner there were obtained U 1 tert-Butyl (3RS,4SR)-3-(4-(5-methoxy-2-methoxymethoxy-benzoyl)-benzoyloxy]-4-(4-methoxymethoxy-3,5-dimethyl-benzoylamino)-pyrrolidine-1-carboxylate, colourless foam, from tert-butyl (3RS,4SR)-3-azido-4-[4-(5-methoxy-2-methoxymethoxy-benzoyl)-benzoyloxy]-pyrrolidine-1-carboxylate (V1) and 4-methoxymethoxy-3,5-dimethylbenzoic acid U 2 tert-Butyl (3RS,4RS)-3-[4-(5-methoxy-2-methoxymethoxy-benzoyl)-benzoyloxy]-4-(4-methoxymethoxy-3,5-dimethyl-benzoylamino)-pyrrolidine-1-carboxylate, colourless foam, from tert-butyl (3RS,4RS)-3-azido-4-(4-(5-methoxy-3-methoxymethoxy-benzoyl)-benzoyloxyl-pyrrolidine-1-carboxylate (V2) and 4-methoxymethoxy-3,5-dimethylbenzoic acid U 3 tert-Butyl (3RS,4RS)-3-[4-(5-methoxy-2-methoxymethoxy-benzoyl)-benzoyloxy]-4-(4-methoxymethoxy-benzoylamino)-pyrrolidine-1-carboxylate, colourless foam, from tert-butyl (3RS,4RS)-3-azido-4-[4-(5-methoxy-3-methoxymethoxy-benzoyl)-benzoyloxy]-pyrrolidine-1-carboxylate (V2) and 4-methoxymethoxy-benzoic acid U 4 tert-Butyl (3RS,4RS)-3-[4-(2-fluoro-3-methoxy-6-methoxymethoxy-benzoyl)-benzoyloxy]-4-(4-methoxymethoxy-3,5-dimethyl-benzoylamino)-pyrrolidine-1-carboxylate from tert-butyl (3RS,4RS)-3-azido-4-[4-(2-fluoro-3-methoxy-6-methoxymethoxy-benzoyl)-benzoyloxy]-pyrrolidine-1-carboxylate (V3) and 4-methoxymethoxy-3,5-dimethyl-benzoic acid U 5 tert-Butyl (3RS,4RS)-3-[4-(2-fluoro-3-methoxy-6-methoxy-methoxy-benzoyl)-benzoyloxy]-4-pyridin-4-ylcarbonylamino-pyrrolidine-1-carboxylate (Ro 48-4206), colourless foam, from tert-butyl (3RS,4RS)-3-azido-4-[4-(2-fluoro-3-methoxy-6-methoxymethoxy-benzoyl)-benzoyloxy]-pyrrolidine-1-carboxylate (V3), from isonicotinic acid U 6 tert-Butyl (3RS,4RS)-3-[4-(2-fluoro-3-methoxy-6-methoxy-methoxy-benzoyl)-benzoyloxy ]-4-(4- methoxymethoxy-benzoylamino)-pyrrolidine-1-carboxylate, colourless foam, from tert-butyl (3RS,4RS)-3-azido-4-[4-(2-fluoro-3-methoxy-6-methoxymethoxy-benzoyl)-benzoyloxy]-pyrrolidine-1-carboxylate (V3) and 4-methoxymethoxy-benzoic acid 4-methoxymethoxy-benzoic acid U 7 tert-Butyl (3RS,4RS)-3-[4-(6-methoxymethoxy-1,3-benzodioxol-5-ylcarbonyl)-benzoyloxy]-4-(4-methoxymethoxy-benzoylamino)-pyrrolidine-1-carboxylate from tert-butyl (3RS,4RS)-3-azido-4-[4-(6-methoxymethoxy-1,3-benzodioxol-5-ylcarbonyl)-benzoyloxy]-pyrrolidine-1-carboxylate (V4) and 4-methoxymethoxy-benzoic acid U 8 tert-Butyl (3R,4R)-3-(4-methoxymethoxy-benzoylamino)-4-[4-(5-methoxy-2-methoxymethoxy-benzoyl)-benzyloxy]-azepane-1-carboxylate, colourless oil, from tert-butyl (3R,4R)-3-azido-4-[4-(5-methoxy-2-methoxymethoxy-benzoyl)-benzyloxy-azepane-1-carboxylate (W) and 4-methoxymethoxy-benzoic acid 9 tert-Butyl (3R,4R)-3-(5-methoxy-2-methoxymethoxy-benzoylamino)-4-[4-(5-methoxy-2-methoxymethoxy-benzoyl)-benzyloxy]-azepane-1-carboxylate, colourless oil, from tert-butyl (3R,4R)-3-azido-4-[4-(5-methoxy-2-methoxymethoxy-benzoyl)-benzyloxy]-azepane-1-carboxylate (W) and 5-methoxy-2-methoxymethoxy-benzoic acid Example V V. The azides used in Examples (U1) to (U7) were prepared by esterifying the alcohol group of tert-butyl (3RS,4RS)-3-azido-4-hydroxy-pyrrolidine-1-carboxylate with an acid of Example (C)

method a) under conditions of the Mitsunobu reaction; or method b) with activation by sulphonyl chloride or carbodiimide.

The following compounds were thus-prepared:

V 1 (Method a) tert-Butyl (3RS,4SR)-3-azido-4-[4-(5-methoxy-2-methoxymethoxy-benzoyl)-benzoyloxy]-pyrrolidine-1-carboxylate from 4-(5-methoxy-2-methoxymethoxy-benzoyl)-benzoic acid (C7)

V 2 (Method b) tert-Butyl (3RS,4RS)-3-azido-4-[4-(5-methoxy-2-methoxymethoxy-benzoyl)-benzoyloxy]-pyrrolidine-1-carboxylate from 4-(5-methoxy-2-methoxymethoxy-benzoyl)-benzoic acid (C7)

V 3 (Method b) tert-Butyl (3RS,4RS)-3-azido-4-[4-(2-fluoro-3-methoxy-6-methoxymethoxy-benzoyl)-benzoyloxy]-pyrrolidine-1-carboxylate from 4-(2-fluoro-3-methoxy-6-methoxymethoxy-benzoyl)-benzoic acid (C3).

V 4 (Method b) tert-Butyl (3RS,4RS)-3-azido-4-[4-(6-methoxymethoxy-1,3-benzodioxol-5-ylcarbonyl)-benzoyloxy]-pyrroridine-1-carboxylate from 4-(6-methoxymethoxy-1,3-benzodioxol-5-ylcarbonyl)-benzoic acid (C17).

Example W

W. Compound (W) used in Examples (U8) and (U9) was obtained from tert-butyl (3R,4R)-3-azido-4-(benzyloxy)-hexahydro-1H-azepine-1-carboxylate (see Example (S)) by debenzylation with trifluoroacetic acid to tert-butyl (3R,4R)-3-azido-4-hydroxy-azepane-1-carboxylate and 0-alkylation of this compound with (4-bromomethyl-phenyl)-( 5-methoxy-2-methoxymethoxy-phenyl)-methanone. The latter compound was obtained by the bromination of (4-hydroxymethyl-phenyl)-(5-methoxy-2-methoxymethoxy-phenyl)-methanone (M8).

The following Examples illustrate the invention further.

Example 1

639.7 mg of tert-butyl (3R,4R)-4-[4-(2-fluoro-3-methoxy-6-methoxymethoxy-benzoyl)-benzoyloxy]-3-(4-methoxymethoxy-benzoylamino)-azepane-1-carboxylate were dissolved in 9 ml of dimethoxyethane and 9 ml of isopropanol and, after cooling to 0° C., saturated slowly with HCl gas and stored in a refrigerator for 24 hours. The solvent was removed completely under reduced pressure and the product was triturated with diethyl ether. The suspension obtained was stirred for several hours; the solvent was decanted off and, after the addition of a further amount of fresh solvent, the stirring was continued overnight. The product was filtered off, washed several times with diethyl ether and dried at 0.1 mbar and 50° C. There were obtained 479 mg of 4-(2-fluoro-6-hydroxy-3-methoxy-benzoyl)-benzoic acid (3R,4R)-3-(4-hydroxy-benzoylamino)-azepan-4-yl ester hydrochloride (1:1) as a yellow powder.

MS: m/e =523.1 (M+H)$^+$

IR (KBr): 1720, 1638, 1607 cm$^{-1}$

The compounds of Examples 2-76 were obtained in an analogous manner:

Example 2

4-(2-Fluoro-6-hydroxy-3-methoxy-benzoyl)-benzoic acid (3R,4R)-3-(4-hydroxy-3-methoxy-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]-3-(3-methoxy-4-methoxymethoxy-benzoylamino)-azepane-1-carboxylate.

MS: m/e=553.3 (M+H)$^+$

IR (KBr): 1721, 1641, 1600 cm$^{-1}$

Example 3

4-(2-Fluoro-6-hydroxy-3-methoxy-benzoyl)-benzoic acid (3R,4R)-3-(4-hydroxy-3,5-dimethoxy-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]-3-(3,5-dimethoxy-4-methoxymethoxy-benzoylamino)-azepane-1-carboxylate MS: m/e=583.2 (M+H)$^+$ IR (KBr): 1720, 1642, 1605 cm$^{-1}$ Example 4

4-(2-Fluoro-6-hydroxy-3-methoxy-benzoyl)-benzoic acid (3R,4R)-3-(3,5-dihydroxy-naphthalen-2-ylcarbonylamino)-azepan-4-yl ester hydrochloride (1:1) as a yellow powder from tert-butyl (3R,4R)-4-[4-(2-fuoro-3-methoxy-6-methoxymethoxy-benzoyl)-benzoyloxy]-3-(3,5-bis-methoxymethoxy-naphthalen-2-ylcarbonylamino)-azepane-1-carboxylate.

MS: 589.5 (M+H)$^+$

IR: 3392, 3269, 1722, 1655, 1622, 1573, 1530, 1501 cm$^{-1}$

Example 5

4-(3-Hydroxy-naphtalen-2-ylcarbonyl)-benzoic acid (3R,4R)-3-(4-hydroxy-3,5-dimethoxy-benzoylamino)-azepan-4-yl ester hydrochloride (1:1) as a yellow powder from tert-butyl (3R,4R)-3-(3,5-dimethoxy-4-methoxymethoxy-benzoylamino)-4-[4-(3-methoxymethoxy-naphthalen-2-ylcarbonyl)-benzoyloxy]-azepane-1-carboxylate.

MS: 585.3 (M+H)+
IR: 3413, 2778, 1721, 1642, 1599, 1540, 1505 cm⁻¹

Example 6

4-(2-Hydroxy-5-methoxy-benzoyl)-benzoic acid (3R,4R)-3-(3,5-dimethoxy-benzoylamino)-azepan-4-yl ester hydrochloride (1:1) as a yellow powder from tert-butyl (3R,4R)-3-(3,5-dimethoxy-benzoylamino)-4-[4-(5-methoxy-2-methoxymethoxy-benzoyl)-benzoyloxy]-azepane-1-carboxylate.

MS: 549.4 (M+H)+
IR: 3421, 1721 1636, 1594, 1273, 1042, 838cm⁻¹

Example 7

4-(2-Fluoro-6-hydroxy-3-methoxy-benzoyl)-benzoic acid (3R,4R)-3-(2-hydroxy-3-methoxy-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy)-3-(3-methoxy-2-methoxymethoxy-benzoylamino)-azepane-1-carboxylate.

MS: m/e=3 553.4 (M+H)+
IR (KBr): 1722, 1642, 1586 cm⁻¹

Example 8

3-(2-Fluoro-6-hydroxy-3-methoxy-benzoyl)-benzoic acid (3R,4R)-3-((3-hydroxy-naphtalen-2-ylcarbonylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]-3-(3-methoxymethoxy-naphthalen-2-ylcarbonylamino)-azepane-1-carboxylate.

Example 9

3-(3-Hydroxy-5,6,7,8-tetrahydro-naphtalen-2-ylcarbonyl)-benzoylamino)-azepan-4-yl ester hydrochloride (1:1) as a yellow powder from tert-butyl (3R,4R)-3-(4-methoxymethoxy-benzoyl-amino)-4-[4-(3-methoxymethoxy-5,6,7,8-tetrahydro-naphthaline-2-ylcarbonyl)-benzoyloxy]-azepane-1-carboxylate

MS
IR

Example 10

4-(2-Fluoro-6-hydroxy-3-methoxy-benzoyl)-benzoic acid (3R,4R)-3-(3,5-dimethoxy-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]-3-(3,5-dimethoxy-benzoylamino)-azepane-1-carboxylate.

MS: 565.3 (M–H)⁻
IR: 3405, 1722 1644, 1593, 1275, 1157, 1018, 821 cm⁻¹

Example 11

4-(2-Fluoro-6-hydroxy-3-methoxy-benzoyl)-benzoic acid (3R,4R)-3-(4-hydroxy-2,3,6-trimethyl-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]-3-(4-methoxymethoxy-2,3,6-trimethyl-benzoylamino) azepane1-carboxylate.

MS: m/e=565 (M+H)+
IR (KBr): 1722, 1639 cm⁻¹

Example 12

4-(2,3-Difluoro-6-hydroxy-benzoyl)-benzoic acid (3R,4R)-3-(4-hydroxy-2,3,6-trimethyl-benzoylamino)-azepan-4-yl ester hydrochloride (1:1) as a yellow powder from tert-butyl (3R,4R)-4-[4-(2,3-difluoro-6-methoxymethoxy-benzoyl)-benzoyloxy]-3-(4-methoxymethoxy-2,3,6-trimethyl-benzoylamino)-azepane-1-carboxylate.

MS: m/e=553 (M+H)+
IR (KBr): 1723, 1632 cm⁻¹

Example 13

4-(2,3-Difluoro-6-hydroxy-benzoyl)-benzoic acid (3R,4R)-3-(4-hydroxy-3,5-diisopropyl-benzoylamino)-azepan-4-yl ester hydrochloride (1:1) as a yellow powder from tert-butyl (3R,4R)-4-[4-(2,3-difluoro-6-methoxymethoxy-benzoyl)-benzoyloxy]-3-(3,5-diisopropyl-4-methoxymethoxy-benzoylamino)-azepane-1-carboxylate.

MS: m/e=595.5 (M+H)+
IR (KBr): 1719, 1632, 1602 cm⁻¹

Example 14

4-(2-Hydroxy-5-methoxy-benzoyl)-benzoic acid (3R,4R)-3-(3,4,5-trimethoxy-benzoylamino)-azepan-4-yl ester hydrochloride (1:1) as a yellow powder from tert-butyl (3R,4R)-4-[4-(5-methoxy-2-methoxymethoxy-benzoyl)-benzoyloxy]-3-(3,4,5-trimethoxy-benzoylamino)-azepane-1-carboxylate.

MS: 579.4 (M+H)+, 307.3
IR: 3425, 1717 1635, 1585, 1500, 1276, 1126, 837 cm⁻¹

Example 15

4-(2-Hydroxy-5-dimethylamino-benzoyl)-benzoic acid (3R,4R)-3-(4-hydroxy-benzoylamino)-azepan-4-yl ester hydrochloride (1:2) as a salmon pink powder from butyl (3R,4R)-4-[4-(5-dimethylamino-2-methoxymethoxy-benzoyl)-benzoyloxy]-3-(4-methoxymethoxy-benzoylamino)-azepane-1-carboxylate.

MS: m/e518.5 (M+H)+
IR (KBr): 1719, 1639, 1608 cm⁻¹

Example 16

4-(2-Hydroxy-5-dimethylamino-benzoyl)-benzoic acid (3R,4R)-3-(4-hydroxy-3-methoxy-benzoylamino)-azepan-4-yl ester hydrochloride (1:2) als as a salmon pink powder from tert-butyl (3R,4R)-3-(3-methoxy-4-methoxymethoxy-benzoylamino)-4-[4[-(2-methoxymethoxy-5-dimethylamino-benzoyl)-benzoyloxy]-azepane-1-carboxylate.

MS: m/e=548.4 (M+H)+
IR (KBr): 1717, 1638, 1605 cm⁻¹

Example 17

4-(2-Hydroxy-5-dimethylamino-benzoyl)-benzoic acid (3R,4R)-3-(4-hydroxy-3,5-diisopropyl-benzoylamino)-azepan-4-yl ester hydrochloride (1:2) as a salmon pink powder from tert-butyl (3R,4R)-3-(3,5-diisopropyl-4-methoxymethoxy-benzoylamino)-4-[4-(2-methoxymethoxy-5-dimethylamino-benzoyl)-benzoyloxy]-azepane-1-carboxylate.

MS: m/e=602.6 (M+H)+
IR (KBr): 1720, 1637, 1606 cm⁻¹

Example 18

4-(7-Hydroxy-1,4-benzodioxin-6-ylcarbonyl)-benzoic acid (3R,4R)-3-(4-hydroxy-benzoylamino)-azepan-4-yl ester hydrochloride (1:1) as a yellow powder from tert-butyl (3R,4R)-4-[4-(2,3-dihydro-1,4-benzodioxin-6-ylcarbonyl)-benzoyloxy]-3-(4-methoxymethoxy-benzoylamino)-azepane-1-carboxylate.

MS: 533.4 (M+H)$^+$
IR: 3417, 3275, 1720, 1639, 1608, 1539, 1502 cm$^{-1}$

Example 19

4-[2-Hydroxy-5-(t-methoxy-ethyl)-benzoyl]-benzoic acid (3R,4R)-3-(4-hydroxy-benzoylamino)-azepan-4-yl ester hydrochloride (1:1) as a light yellow powder from tert-butyl (3R,4R)-4-[4-[5-(1-methoxyethyl)-2-methoxymethoxy-benzoyl]-benzoyloxy]-3-(4-methoxymethoxy-benzoylamino)-azepane-1-carboxylate.

MS: 533.4 (M+H)$^+$
IR: 3424m 1680, 1565, 1506 cm$^{-1}$

Example 20

4-(2-Fluoro-6-hydroxy-3-methoxy-benzoyl)-benzoic acid (3 R,4R)-3-(4-hydroxy-3,5-dimethyl-benzoylamino)-azepan-4-yl ester hydrochloride (1:1) as a yellow powder from tert-butyl (3R,4R)-4-[4-(2-fluoro-3-methoxy-6-methoxymethoxy-benzoyl)-benzoyloxy]- 3-(4-methoxymethoxy-3,5-dimethyl-benzoylamino)-azepane-1-carboxylate.

MS: m/e=549.5 (M+H)$^+$
IR (KBr): 1722, 1642, 1605 cm$^{-1}$

Example 21

4-(2-Hydroxy-5-dimethylamino-benzoyl)-benzoic acid (3R,4R)-3-(4-hydroxy-3,5-dimethyl-benzoylamino)-azepan-4-yl ester hydrochloride (1:2) as a salmon pink powder from tert-butyl (3R,4R)-4-[4-(2-methoxymethoxy-5-dimethylamino-benzoyl)-benzoyloxy]-3-(4-methoxymethoxy-3,5-dimethyl-benzoylamino)-azepane-1-carboxylate.

MS: m/e=544.5 (M–H)$^-$
IR (KBr): 1720, 1638, 1605 cm$^{-1}$

Example 22

4-(2-Fluoro-6-hydroxy-4-methoxy-benzoyl)-benzoic acid (3R,4R)-3-(4-hydroxy-3,5-diisopropyl-benzoylamino)-azepan-4-yl ester hydrochloride (1:1) as a colourless powder from tert-butyl 3R,4R)-4-[4-(2-fluoro-4-methoxy-6-methoxymethoxy-benzoyl)-benzoyloxy]-3-(3,5-diisopropyl-4-methoxymethoxy-benzoylamino)-azepane-1-carboxylate.

MS: m/e=605.4 (M–H)$^-$
IR (KBr): 1722, 1639, 1600 cm$^{-1}$

Example 23

4-(2-Hydroxy-5-methoxy-benzoyl)-benzoic acid (3R,4R)-3-(3-acetyl-4-hydroxy-benzoylamino)-azepan-4-yl ester hydrochloride (1:1) as a yellow powder from tert-butyl (3R,4R)-3-(3-acetyl-4-methoxymethoxy-benzoylamino)-4-[4-(5-methoxy-2-methoxymethoxy-benzoyl)-benzoyloxy]-azepane-1-carboxylate.

MS: 547.7 (M+H)$^+$
IR: 3429, 1717 1642, 1608, 1533, 1484, 1282, 1040, 826 cm$^{-1}$

Example 24

4-(6-Hydroxy-quinolin-7-ylcarbonyl)-benzoic acid (3R,4R)-3-(4-hydroxy-benzoylamino)-azepan-4-yl ester hydrochloride (1:1) as a yellow powder from tert-butyl (3R,4R)-3-(4-methoxymethoxy-benzoylamino)-4-[4-(6-methoxymethoxy-quinolin-7-ylcarbonyl)-benzoyloxy]-azepane-1-carboxylate.

MS: m/e=539.4 (M+H)$^+$
IR (KBr): 1720, 1634, 1605 cm$^{-1}$

Example 25

4-(2,3-Difluoro-6-hydroxy-benzoyl)-benzoic acid (3R,4R)3-(4-hydroxy-3,5-dimethyl-benzoylamino)-azepan-4-yl ester hydrochloride (1:1) as a light yellow powder from tert-butyl (3R,4R)-4-[4-(2,3-difluoro-6-methoxymethoxy-benzoyl)-benzoyloxy]-3-(4-methoxymethoxy-3,5-dimethyl-benzoylamino)-azepane-1-carboxylate.

MS: m/e=539.4 (M+H)$^+$
IR (KBr): 1720, 1634, 1605 cm$^{-1}$

Example 26

4-(2,4-Difluoro-6-hydroxy-benzoyl)-benzoic acid (3R,4R)-3-(4-hydroxy-3,5-dimethyl-benzoylamino)-azepan-4-yl ester hydrochloride (1:1) as a colourless powder from tert-butyl (3R,4R)-4-[4-(2,4-difluoro-6-methoxymethoxy-benzoyl)-benzoyloxy]-3-(4-methoxymethoxy- 3,5-dimethyl-benzoylamino)-azepane-1-carboxylate.

MS: m/e=539.5 (M+H)$^+$
IR (KBr): 1718, 1635, 1608 cm$^{-1}$

Example 27

4-(2-Hydroxy-5-methoxy-benzoyl)-benzoic acid (3R,4R)-3-(3,5-diethoxy-benzoylamino)-azepan-4-yl ester hydrochloride (1:1) as a yellow powder from tert-butyl (3R,4R)-3-(3,5-diethoxy-benzoylamino)-4-[4-(5-methoxy-2-methoxymethoxy-benzoyl)-benzoyloxy]-azepane-1-carboxylate.

MS: 577.4 (M+H)$^+$, 305.7, 193.5
IR: 3404, 1721, 1636, 1593, 1531, 1484, 1273, 1058, 831 cm$^{-1}$

Example 28

4-(4-Hydroxy-biphenyl-3-ylcarbonyl)-benzoic acid (3R,4R)-3-(4-hydroxy-benzoylamino)-azepan-4-yl ester hydrochloride (1:1) as a yellow powder from tert-butyl (3R,4R)-3-(4-methoxymethoxy-benzoylamino)-4-[4-(4-methoxymethoxy-biphenyl-3-ylcarbonyl)-benzoyloxy]-azepane-1-carboxylate.

MS: 551.3 (M+H)$^+$
IR: 3255, 2796, 1722, 1631, 1607, 1539, 1505 cm$^{-1}$

Example 29

4-(6-Hydroxy-quinolin-7-ylcarbonyl)-benzoic acid (3R,4R)-3-(4-hydroxy-3,5-dimethyl-benzoylamino)-azepan-4-yl ester hydrochloride (1:1) as a yellow powder from tert-butyl (3R,4R)-3-(4-methoxymethoxy-3,5-dimethyl-benzoylamino)-4-[4-(6-methoxymethoxy-chinolin-7-ylcarbonyl)-benzoyloxy]-azepane-1-carboxylate.

MS: 554.5 (M+H)$^+$
IR: 3411, 1720, 1639, 1606, 1536, 1485 cm$^{-1}$

Example 30

4-(5-Acetyl-2-hydroxy-benzoyl)-benzoic acid (3R,4R)-3-(4-hydroxy-benzoylamino)-azepan-4-yl ester hydrochloride (1:1) as a yellow powder from tert-butyl (3R,4R)-4-[4-(5- acetyl-2-methoxymethoxy-benzoyl)-benzoyloxy]-3-(4-methoxymethoxy-benzoylamino)-azepane-1-carboxylate.

MS: 517.3 (M+H)$^+$

IR: 3410, 1722, 1628, 1606 cm$^{-1}$

Example 31

4-(2-Hydroxy-10-methyl-phenothiazin-1-ylcarbonyl)-benzoic acid (3R,4R)-3-(4-hydroxy-benzoylamino)-azepan-4-yl ester hydrochloride (1:2) as an orange powder from tert-butyl (3R,4R)-3-(4-methoxymethoxy)-benzoylamino)-4-[4-(3-methoxymethoxy-10-methyl-phenothiazin-2-ylcarbonyl)-benzoyl]-azepane-1-carboxylate.

MS: 610.4 (M+H)$^+$

IR: 3376, 2669, 1723, 1612, 1540, 1507, 1268, 849, 822, 755.

Example 32

4-(2-Fluoro-6-hydroxy-3-methoxy-benzoyl)-benzoic acid (3R,4R)-3-(3,5-diethyl-4-hydroxy-benzoylamino)-azepan-4-yl ester hydrochloride (1:1) as a yellow powder from tert-butyl (3R,4R)-3-(3,5-diethyl-4-methoxymethoxy-benzoylamino)-4-[2-fluoro-3-methoxy-6-methoxymethoxy-benzoyl)-benzoyloxy]-azepane-1-carboxylate.

MS: m/e=579.5 (M+H)$^+$

IR (KBr): 1722, 1639, 1603 cm$^{-1}$

Example 33

4-(2,3-Difluoro-6-hydroxy-benzoyl)-benzoic acid (3R,4R)-3-(3,5-diethyl-4-hydroxy-benzoylamino)-azepan-4-yl ester hydrochloride (1:1) as a light yellow powder from tert-butyl (3R,4R)-3-(3,5-diethyl-4-methoxymethoxy-benzoylamino)-4-[4-(2,3-difluoro-6-methoxymethoxy-benzoyl)-benzoyloxy]-azepane-1-carboxylate.

MS: m/e=567.4 (M+H)$^+$

IR (KBr): 1722, 1634, 1604 cm$^{-1}$

Example 34

4-(2-Hydroxy-5-dimethylamino-benzoyl)-benzoic acid (3R,4R)-3-(3,5-diethyl-4-hydroxy-benzoylamino)-azepan-4-yl ester hydrochloride (1:2) as a salmon pink powder from tert-butyl (3R,4R)-3-(3,5-diethyl-4-methoxymethoxy-benzoylamino)-4-[4-(2-methoxymethoxy-5-dimethylamino-benzoyl)-benzoyloxy]-azepane-1-carboxylate.

MS: m/e=574.5 (M+H)$^+$

IR (KBr): 1720, 1638, 1605 cm$^{-1}$

Example 35

4-(2,4-Difluoro-6-hydroxy-benzoyl)-benzoic acid (3R,4R)-3-(3,5-diethyl-4-hydroxy-benzoylamino)-azepan-4-yl ester hydrochloride (1:1) as a colourless powder from tert-butyl (3R,4R)- 3-(3,5-diethyl-4-methoxymethoxy-benzoylamino)-4-[4-(2,4-benzoyloxy-azepane-1-carboxylate.

MS: m/e=567.4 (M+H)$^+$

IR (KBr): 1722, 1636, 1603 cm$^{-1}$

Example 36

4-(2-Hydroxy-5-methoxy-benzoyl)-benzoic acid (3R,4R)-3-(4-hydroxy-3,5-dimethyl-benzoylamino)-azepan-4-yl ester hydrochloride (1:1) as a yellow powder from tert-butyl (3R,4R)-4-[4-(5-methoxy-2-methoxymethoxy-benzoyl)-benzoyloxy]-3-(4-methoxymethoxy-3,5-dimethyl-benzoylamino)-azepane-1-carboxylate.

MS: 531.2 (M+H)$^+$

IR: 3405, 1721, 1636, 1606, 1532, 1485 cm$^{-1}$

Example 37

4-(2-Hydroxy-5-methoxy-benzoyl)-benzoic acid (3R,4R)-3-(4-pyridinoylamino)-azepan-4-yl ester hydrochloride (1:2) as a yellow powder from tert-butyl (3R,4R)-4-[4-(5-methoxy-2-methoxymethoxy-benzoyl)-benzoyloxy]-3-(4-pyridinoylamino)-azepane-1-carboxylate.

MS: 490.4 (M+H)$^+$

IR: 3428, 1723, 1673, 1636, 1606, 1548, 1483, 1269, 831 cm$^{-1}$

Example 38

4-(2-Hydroxy-5-methyl-benzoyl)-benzoic acid (3R,4R)-3-(4-hydroxy-benzoylamino)-azepan-4-yl ester hydrochloride (1:1) as a yellow powder from tert-butyl (3R,4R)-3-(4-methoxymethoxy-benzoylamino)-4-[4-(2-methoxymethoxy-5-methyl-benzoyl)-benzoyloxy]-azepane-1-carboxylate.

MS: 489.2 (M+H)$^+$.

R: 3258, 1721, 1832, 1608, 1540, 1505, 1275, 851.

Example 39

4-(6-Hydroxy-1,3-benzodioxol-5-ylcarbonyl)-benzoic acid 9 (3R,4R)-3-(4-hydroxy-3,5-dimethyl-benzoylamino)-azepan-4-yl ester hydrochloride (1:1) as a yellow powder from tert-butyl (3R,4R)-4-[4-(6-methoxymethoxy-1,3-benzodioxol-5-ylcarbonyl)-benzoyloxy]-3-(4-methoxymethoxy-3,5-dimethyl-benzoylamino)-azepane-1-carboxylate.

MS: 547.4 (M+H)$^+$

IR: 3424, 2771, 1720, 1627, 1603, 1532 cm$^{-1}$

Example 40

4-(2-Hydroxy-5-isopropyl-benzoyl)-benzoic acid (3R,4R)-3-(4-hydroxy-benzoylamino)-azepan-4-yl ester hydrochloride (1:1) as a yellow powder from tert-butyl (3R,4R)-4-[4-(5-isopropyl-2-methoxymethoxy-benzoyl)-benzoyloxy]-3-(4-methoxymethoxy-benzoylamino)-azepane-1-carboxylate.

MS: 517.2 (M+H)$^+$.

IR: 3398, 1723, 1831, 1607, 1539, 1505, 1276, 840.

Anal. calc. for $C_{30}H_{32}N_2O_6.HCl.H_2O$ (Wa 2.33) (553.055): C 65.15, H 6.01, N 5.07; found : C 65.34, H 6.08, N 4.92.

Example 41

4-(6-Hydroxy-1,4-benzodioxin-1-yl-carbonyl)-benzoic acid (3R,4R)-3-(4-hydroxy-3,5-dimethyl-benzoylamino)-azepan-4-yl ester hydrochloride (1:1) as a yellow powder from tert-butyl (3R,4R)-4[4-(6-methoxymethoxy-(1,4-benzodioxin-5-ylcarbonyl)-benzoyloxy]-3-(4-methoxymethoxy-3,5-dimethyl-benzoylamino)-azepane-1-carboxylate.

MS: 561.4 (M+H)$^+$.

IR: 3421, 1720, 1632, 1606, 1740, 1268, 825.

Example 42

4-(2-Fluoro-3-dimethylamino-6-hydroxy-benzoyl)-benzoic acid (3R,4R)-3-(4-hydroxy-benzoylamino)-azepan- 4-yl ester hydrochloride (1:2) as a colourless powder from tert-butyl (3R,4R)-4-[4-(2-fluoro-3-dimethylamino-6-methoxymethoxy-benzoyl)-benzoyloxy]-3-(4-methoxymethoxy-benzoylamino)-azepane-1-carboxylate.

MS: m/e=536.4 (M+H)$^+$

IR (KBr): 1721, 1631, 1607 cm$^{-1}$

Example 43

4-(2-Fluoro-6-hydroxy-3-dimethylamino-benzoyl)-benzoic acid (3R,4R)-3-(4-hydroxy-3,5-dimethyl-benzoylamino)-azepan-4-yl ester hydrochloride (1:2) as a yellow powder from tert-butyl (3R,4R)-4-[4-(2-fluoro-6-methoxymethoxy-3-dimethylamino-benzoyl)-benzoyloxy]-3-(4-methoxymethoxy-3,5-dimethyl-benzoyl-amino)-azepane-1-carboxylate.

MS: m/e=564.4 (M+H)$^+$

IR (KBr): 1721, 1631, 1604 cm$^{-1}$

Example 44

4-(2-Fluoro-6-hydroxy-3-dimethylamino-benzoyl)-benzoic acid (3R,4R)-3-(4-hydroxy-3,5-dimethoxy-benzoylamino)-azepan-4-yl ester hydrochloride (1:2) as a colourless powder from tert-butyl (3R,4R)-4-[4-(2-fluoro-6-methoxymethoxy-3-dimethylamino-benzoyl)-benzoyloxy]-3-(3,5-dimethoxy-4-methoxymethoxy-benzoylamino)-azepane-1-carboxylate.

MS: m/e=596.4 (M+H)$^+$

IR (KBr): 1721, 1631, 1603 cm$^{-1}$

Example 45

4-(5-Acetyl-2-hydroxy-benzoyl)-benzoic acid (3R,4R)-3-(4-hydroxy-3,5-dimethoxy-benzoylamino)-azepan-4-yl ester hydrochloride (1:1) as a yellow powder from tert-butyl (3R,4R)-4-[4-(5-acetyl-2-methoxymethoxy-benzoyl)-benzoyloxy]-3-(4-methoxymethoxy-3,5-dimethyl-benzoylamino)-azepane-1-carboxylate.

MS: 545 (M+H)$^+$

IR: 3399, 1721, 1673, 1628, 1601 cm$^{-1}$

Example 46

4-(2-Fluoro-6-hydroxy-3-methoxy-benzoyl)-benzoic acid (3R,4R)-3-(4-pyridinoylamino)-azepan-4-yl ester hydrochloride (1:2) as a yellow powder from tert-butyl (3R,4R)-4-[4-(2-fluoro-3-methoxy-6-methoxymethoxy-benzoyl)-benzoyloxy]-3-(4-pyridinoylamino)-azepane-1-carboxylate.

MS: 508.3 (M+H)$^+$

IR: 3429, 1724, 1672, 1640, 1608, 1550, 1499, 1276, 840 cm$^{-1}$

Example 47

4-(2-Hydroxy-5-methoxy-benzoyl)-benzoic acid (3R,4R)-3-(3-tert-butyl-4-hydroxy-benzoylamino)-azepan-4-yl ester hydrochloride (1:1) as a yellow powder from tert-butyl (3R,4R)-3-(3-tert-butyl-4-hydroxy-benzoylamino)-4-[4-(5-methoxy-2-methoxymethoxy-benzoyl)-benzoyloxy]-azepane-1-carboxylate.

MS: 561.4 (M+H)$^+$

IR: 3426, 1740, 1635, 1604, 1537, 1485, 1261 cm$^{-1}$

Example 48

4-(2-Fluoro-6-hydroxy-3-methoxy-benzoyl)-benzoic acid (3R,4R)-3-(3-bromo-4-hydroxy-benzoylamino)-azepan-4-yl ester hydrochloride (1:1) as a yellow powder from tert-butyl (3R,4R)-3-(3-bromo-4-methoxymethoxy-benzoylamino)-4-[4-(2-fluoro-3-methoxy-6-methoxymethoxy-benzoyl)-benzoyloxy]-azepane-1-carboxylate.

MS: 599.2 (M−H)$^-$

IR: 3416, 1722, 1642, 1601 cm$^{-1}$

Example 49

4-(2-Hydroxy-5-methoxy-benzoyl)-benzoic acid (3R,4R)-3-(4-hydroxy-3-isopropyl-benzoylamino)-azepan-4-yl ester hydrochloride (1:1) as a yellow powder from tert-butyl (3R,4R)-3-(3-isopropyl-4-methoxymethoxy-benzoylamino)-4-[4-(5-methoxy-2-methoxymethoxy-benzoyl)-benzoyloxy]-azepane-1-carboxylate.

MS: 547.6 (M+H)$^+$

IR: 3421, 1721, 1635, 1604, 1537, 1485, 1277, 832 cm$^{-1}$

Example 50

4-(2-Hydroxy-5-methoxy-benzoyl)-benzoic acid (3R,4R)-3-(4-hydroxy-3-sec-butyl-benzoylamino)-azepan-4-yl ester hydrochloride (1:1) as a yellow powder from tert-butyl (3R,4R)-3-(3-sec-butyl-4-methoxymethoxy-benzoylamino)-4-[4-(5-methoxy-2-methoxymethoxy-benzoyl)-benzoyloxy]-azepane-1-carboxylate.

MS: 561.6 (M+H)$^+$

IR: 3393, 1719, 1636, 1604, 1538, 1485, 1278, 833 cm$^{-1}$

Example 51

4-(2-Fluoro-3-isopropyl-6-hydroxy-benzoyl)-benzoic acid (3R,4R)-3-(4-hydroxy-3,5-dimethyl-benzoylamino)-azepan-4-yl ester hydrochloride (1:1) as a yellow powder from tert-butyl (3R,4R)-4-[4-(2-fluoro-3-isopropyl-6-methoxymethoxy-benzoyl)-benzoyloxy]-3-(4-methoxymethoxy-3,5-dimethyl-benzoylamino)-azepane-1-carboxylate.

MS: 563.4 (M+H)$^+$

IR: 3412, 1722, 1638, 1533 cm$^{-1}$

Example 52

4-(2-Fluoro-6-hydroxy-3-pyrrolidin-1-yl-benzoyl)-benzoic acid (3R,4R)-3-(4-hydroxy-benzoylamino)-azepan-4-yl ester hydrochloride (1:2) as a salmon pink powder from tert-butyl (3R,4R)-4-[4-(2-fluoro-6-methoxymethoxy-3-pyrrolidin-1-yl-benzoyl)-benzoyloxy]-3-(4-methoxymethoxy-benzoylamino)-azepane-1-carboxylate.

MS: m/e=562.6 (M+H)$^+$

IR (KBr): 1721, 1631, 1606 cm$^{-1}$

Example 53

4-(2-Fluoro-6-hydroxy-3-pyrrolidin-1-yl-benzoyl)-benzoic acid (3R,4R)-3-(4-hydroxy-3,5-dimethyl-benzoylamino)-azepan-4-yl ester hydrochloride (1:2) as a salmon pink powder from tert-butyl (3R,4R)-4-[4-(2-fluoro-6-methoxymethoxy-3-pyrrolidin-1-yl-benzoyl)-benzoyloxy]-3-(4-methoxymethoxy-3,5-dimethyl-benzoylamino)-azepane-1-carboxylate.

MS: m/e=590.6 (M+H)$^+$

IR (KBr): 1721, 1631, 1604 cm$^{-1}$

Example 54

4-(2-Fluoro-6-hydroxy-3-methyl-benzoyl)-benzoic acid (3R, 4R)-3-(4-hydroxy-benzoylamino)-azepan-4-yl ester hydrochloride (1:1) as a beige powder from tert-butyl (3R,4R)-3-(4-methoxymethoxy)-benzylamino)-4-[4-(2-fluoro-6-methoxymethoxy-3-methyl-benzoyl)-benzoyloxy]-azepane-1-carboxylate.

MS: 505.3 (M+H)+
IR: 3415, 1721, 1604, 1471, 1276, 1276, 850.

Example 55

4-(3-Ethyl-2-fluoro-6-hydroxy-benzoyl)-benzoic acid (3R, 4R)-3-(4-hydroxy-benzoylamino)-azepan-4-yl ester hydrochloride (1:1) as a beige powder from tert-butyl (3R,4R)-4-[4-(3-ethyl-2-fluoro-6-methoxymethoxy-benzoyl)-benzoyloxy]-3-(4-methoxymethoxy-3,5-dimethyl-benzoylamino)azepane-1-carboxylate.

MS :549.6 (M+H)+.
IR: 3401, 1722, 1639, 1604, 1533, 1485, 1273, 1219, 827.

Example 56

4-(2-Fluoro-6-hydroxy-3-piperidin-1-yl-benzoyl)-benzoic acid (3R,4R)-3-(4-hydroxy-3,5-dimethyl-benzoylamino)-azepan-4-yl ester hydrochloride (1:2) as a beige powder from tert-butyl (3R,4R)-4-[4-(2-fluoro-6-methoxymethoxy-3-piperidin-1-yl-benzoyl)-benzoyloxy]-3-(4-methoxymethoxy-3,5-dimethyl-benzoylamino)-azepane-1-carboxylate.

MS: 604.6 (M+H)+
IR: 1720, 1673, 1630, 1534 cm$^{-1}$

Example 57

4-(2-Fluoro-6-hydroxy-4-methoxy-benzoyl)-benzoic acid (3R,4R)-3-(4-hydroxy-benzoylamino)-azepan-4-yl ester hydrochloride (1:1) as a colourless powder from tert-butyl (3R,4R)-4-[4-(2-(2-fluoro-4-methoxy-6-methoxymethoxy-benzoyl)-benzoyloxy]-3-(4-methoxymethoxy-benzoylamino)-azepane-1-carboxylate.

MS: m/e=523.2 (M+H)+
IR (KBr): 1718, 1639, 1608 cm$^{-1}$

Example 58

4-(2-Fluoro-6-hydroxy-benzoyl)-benzoic acid (3R,4R)-3-(4-hydroxy-3-methoxy-benzoylamino)-azepan-4-yl ester hydrochloride (1:1) as a colourless powder from tert-butyl (3R,4R)-4-[4-(2-fluoro-6-methoxymethoxy-benzoyl)-benzoyloxy]-3-(3-methoxy-4-methoxymethoxy-benzoylamino)-azepane-1-carboxylate.

MS: m/e=523.3 (M+H)+
IR (KBr): 1721, 1634, 1617 cm$^{-1}$

Example 59

4-[4-(2-Fluoro-6-hydroxy)-benzoyl]-benzoic acid (3R,4R)-3-(2-hydroxy-5-methoxy-benzoylamino)-azepan-4-yl ester hydrochloride (1:1) as a yellow powder from tert-butyl (3R,4R)-4-[4-(2-fluoro-6-methoxymethoxy-benzoyl)-benzoyloxy]-3-(5-methoxy-2-methoxymethoxy-benzoylamino)-azepane-1-carboxylate.

MS: 523.1 (M+H)+
IR: 3405, 3296, 1718, 1637, 1617, 1542, 1495 cm$^{-1}$

Example 60

4-(3-Hydroxy-naphthalen-2-ylcarbonyl)-benzoic acid (3R,4R)-3-(4-hydroxy-benzoylamino)-azepan-4-yl ester hydrochloride (1:1) as a yellow powder from tert-butyl (3R,4R)-3-[4-(tert-butyl-dimethylsilanyloxy)-benzoylamino]-4-(3-methoxymethoxy-naphthalen-2-ylcarbonyl)-benzoyloxy)-azepane-1-carboxylate.

MS: 525.4 (M+H)+
IR: 3243, 1721, 1642, 1605, 1537, 1505 cm$^{-1}$

Example 61

4-(2-Fluoro-6-hydroxy-4-methoxy-benzoyl)-benzoic acid (3 R,4R)-3-(4-hydroxy-3,5-dimethoxy-benzoylamino)-azepan-4-yl ester hydrochloride (1:1) as a colourless powder from tert-butyl (3R,4R)-4-[4-(2-fluoro-4-methoxy-6-methoxymethoxy-benzoyl)-benzoyloxy]-3-(3,5-dimethoxy-4-methoxymethoxy-benzoylamino)-azepane-1-carboxylate.

MS: m/e=583.2 (M+H)+
IR (KBr): 1721, 1639, 1604 cm$^{-1}$

Example 62

4-(2-Fluoro-6-hydroxy-benzoyl)-benzoic acid (3R,4R)-3-(4-hydroxy-3,5-dimethoxy-benzoylamino)-azepan-4-yl ester hydrochloride (1:1) as a colourless powder from tert-butyl (3R,4R)-4-[4-(2-fluoro-6-methoxymethoxy-benzoyl)-benzoyloxy]-3-(3,5-dimethoxy-4-methoxymethoxy-benzoylamino)-azepane-1-carboxylate.

MS: m/e=553.2 (M+H)+
IR (KBr): 1722, 1630, 1615 cm$^{-1}$

Example 63

4-(2,3-Difluoro-6-hydroxy-benzoyl)-benzoic acid (3R, 4R)-3-(4-hydroxy-3,5-dimethoxy-benzoylamino)-azepan-4-yl ester hydrochloride (1:1) as a light yellow powder from tert-butyl (3R,4R)-4-[4:-(2,3-difluoro-6-methoxymethoxy-benzoyl)-benzoyloxy]-3-(3,5-dimethoxy-4-methoxymethoxy-benzoylamino)-azepane-1-carboxylate.

MS: m/e=571.3 (M+H)+
IR (KBr): 1722, 1647, 1606 cm$^{-1}$

Example 64

4-(2,4-Difluoro-6-hydroxy-benzoyl)-benzoic acid (3R, 4R)-3-(4-hydroxy-3,5-dimethoxy-benzoylamino)-azepan-4-yl ester hydrochloride (1:1) as a colourless powder from tert-butyl (3R,4R)-4-[4-(2,4-difluoro-6-methoxymethoxy-benzoyl)-benzoyloxy]-3-(3,5-dimethoxy-4-methoxymethoxy-benzoylamino)-azepane-1-carboxylate.

MS: m/e=571.2 (M+H)+
IR (KBr): 1722, 1640, 1609 cm$^{-1}$

Example 65

4-(2-Hydroxy-5-methoxy-benzoyl)-benzoic acid (3R, 4R)-3-(5-fluoro-2-hydroxy-benzoylamino)-azepan-4-yl ester hydrochloride (1 :1) as a yellow powder from tert-butyl (3R,4R)-3-(5-fluoro-2-hydroxy-benzoylamino)-4-[4-(5-methoxy-2-methoxy-methoxy-benzoyl)-benzoyloxy]-azepane-1-carboxylate.

MS: 523.2 (M+H)+
IR: 3406, 1720, 1636, 1609, 1485, 1274, 1228, 826 cm$^{-1}$

Example 66

3,5-Difluoro-4-(2-hydroxy-5-methoxy-benzoyl)-benzoic acid (3R,4R)-3-(4-hydroxy-benzoylamino)-azepan-4-yl ester hydrochloride (1:1) as a yellow powder from tert-butyl (3R,4R)-4-[3,5-difluoro-4-(5-methoxy-2-methoxymethoxy-benzoyl)-benzoyloxy]-3-(4-hydroxy-benzoylamino)-azepane-1-carboxylate.

MS: 541.3 (M+H)+

IR: 217.1, 109.1: IR: 3411, 1729, 1636, 1609, 1484, 1223, 1035 852 cm⁻¹

Example 67

4-(2-Hydroxy-5-methylthio-benzoyl)-benzoic acid (3R,4R)-3-(4-hydroxy-benzoylamino)-azepan-4-yl ester hydrochloride (1:1) as a yellow powder from tert-butyl (3R,4R)-3-(4-hydroxybenzoylamino)-4-[4-(2-methoxymethoxy-5-methylthio-benzoyl)-benzoyloxy]-azepane-1-carboxylate.

MS: 519.3 (M–H)⁻

IR: 3403, 1721, 1627, 1606, 1540, 1277, 1017, 829 cm⁻¹

Example 68

4-(2-Hydroxy-5-methoxy-benzoyl)-benzoic acid (3RS,4RS)-4-(4-hydroxy-3,5-dimethyl-benzoylamino)-pyrrolidin-3-yl ester hydrochloride (1:1) as a yellow powder from tert-butyl (3RS,4RS)-3-(4-(5-methoxy-2-methoxymethoxy-benzoyl)-benzoyloxy]-4-(4-methoxymethoxy-3,5-dimethyl-benzoylamino)-pyrrolidine-1-carboxylate.

MS: 505.3 (M+H)+

IR: 3387, 3269, 1728, 1638, 1606, 1533 cm⁻¹

Example 69

4-(2-Hydroxy-5-methoxy-benzoyl)-benzoic acid (3RS,4RS)-4-(4-hydroxy-benzoylamino)-pyrrolidin-3-yl ester hydrochloride (1:1) as a yellow powder from tert-butyl (3RS,4RS)-3-[4-(5-methoxy-2-methoxymethoxy-benzoyl)-benzoyloxy]-4-(4-methoxymethoxy-benzoylamino)-pyrrolidine-1-carboxylate.

MS: 477.3 (M+H)+

IR: 3417, 1727, 1637, 1608 cm⁻¹

Example 70

4-(2-Hydroxy-5-methoxy-benzoyl)-benzoic acid (3RS,4SR)-4-(4-hydroxy-3,5-dimethyl-benzoylamino)-pyrrolidin-3-yl ester hydrochloride (1:1) as a yellow powder from tert-butyl (3RS,4SR)-3-[4-(5-methoxy-2-methoxymethoxy-benzoyl)-benzoyloxy]-4-(4-methoxymethoxy-3,5-dimethyl-benzoylamino)-pyrrolidine-1-carboxylate.

MS: 505.4 (M+H)+

IR: 3415, 1716, 1650, 1605, 1540, 1486 cm⁻¹

Example 71

4-(2-Fluoro-6-hydroxy-3-methoxy-benzoyl)-benzoic acid (3RS,4RS)-4-(4-hydroxy-3,5-dimethyl-benzylamino)-pyrrolidin-3-yl ester hydrochloride (1:1) as a yellow powder from tert-butyl (3RS,4RS)-3-[4-(2-fluoro-3-methoxy-6-methoxymethoxy-benzoyl)-benzoyloxy]-4-(4-methoxymethoxy-3,5-dimethyl-benzoylamino)-pyrrolidin-1-carboxylate MS: 523.4 (M+H)+ IR: 3399, 2736, 1729, 1643, 1605, 1534, 1484 cm⁻¹

Example 72

4-(2-Fluoro-6-hydroxy-3-methoxy-benzoyl)-benzoic acid (3RS,4RS)-4-pyridin-4-ylcarbonylamino-pyrrolidin-3-yl ester hydrochloride (1:2) as a yellow powder from tert-butyl (3RS,4RS)-3-[4-(2-fluoro-3-methoxy-6- methoxymethoxy-benzoyl)-benzoyloxy]-4-pyridin-4-ylcarbonylamino-pyrrolidine-1-carboxylate (Ro 48–4206).

MS: 480.3 (M+H)+

IR: 3431, 1727, 1693, 1538, 1491 cm⁻¹

Example 73

4-(2-Hydroxy-5-methoxy-benzoyl)-benzoic acid (3RS,4RS)-4-(4-hydroxy-benzoylamino)-pyrrolidin-3-yl ester hydrochloride (1:1) as a yellow powder from tert-butyl (3RS,4RS)-3-[4-(2-fluoro-3-methoxy-6-methoxymethoxy-benzoyl)-benzoyloxy]-4-(4-methoxymethoxy-benzoylamino)-pyrrolidine-1-carboxylate.

MS: 495.3 (M+H)+

IR: 3417, 3261, 1728, 1643, 1608, 1539, 1504 cm⁻¹

Example 74

4-(6-Hydroxy-1,3-benzodioxol-5-ylcarbonyl)-benzoic acid (3RS,4RS)-4-(4-hydroxy-3,5-dimethyl-benzoylamino)-pyrrolidin-3-yl ester hydrochloride (1:1) as a yellow powder from tert-butyl (3RS,4RS)-3-[4-(6-methoxymethoxy-1,3-benzodioxol-5-ylcarbonyl)-benzoyloxy]-4-(4-methoxymethoxy-benzoylamino)-pyrrolidine-1-carboxylate.

MS: 519.3 (M+H)+

IR: 3416, 1726, 1700, 1641, 1603, 1530, 1249, 1038 cm⁻¹

Example 75

(3R,4R)-4-Hydroxy-N-[4-[4-(2-hydroxy-5-methoxy-benzoyl)benzyloxy]-azepan-3-yl]-benzamide hydrochloride (1:1) as a yellow powder from tert-butyl (3R,4R)-3-(4-methoxymethoxy-benzoylamino)-4-[4-(5-methoxy-2-methoxymethoxy-benzoyl)-benzyloxy]-azepane-1-carboxylate.

MS: 491.3 (M+H)+

IR: 3239, 1634, 1607, 1542, 1506, 1483 cm⁻¹

Example 76

(3R,4R)-2-Hydroxy-N-[4-[4-(2-hydroxy-5-methoxy-benzoyl]-azepan-3-yl]-5-methoxy-benzamide hydrochloride (1:1) as a yellow powder from tert-butyl (3R,4R)-3-(5-methoxy-2-methoxymethoxy-benzoylamino)-4-[4-(5-methoxy-2-methoxymethoxy-benzoyl)-benzyloxy]-azepane-1-carboxylate.

MS: 521.5 (M+H)+

IR: 3422, 2939, 1636, 1598, 1542, 1488 cm⁻¹

Example 77

A mixture of 14 mg of 4-(2-hydroxy-5-methoxy-benzoyl)-benzoic acid (3RS,4SR)-4-(4-hydroxy-3,5-dimethylbenzoylamino)-pyrrolidin-3-yl ester hydrochloride (Example 70), 0.01 ml of triethylamine and 37 mg of formamidinesulphonic acid in 2 ml of dimethylformamide was stirred at room temperature for 6 days. The solvent was evaporated under reduced pressure and the residue was taken up in water, sonicated and filtered. After drying under reduced pressure there were obtained 8 mg of 4-(2-hydroxy-5-methoxy-benzoyl)-benzoic acid (3RS,4SR)-1-(amino-imino-methyl)-4-(4-hydroxy-3,5-dimethylbenzoyl amino)-pyrrolidin-3-yl ester as a yellow powder.

MS: 547.5 (M+H)+

Examples AA–FF illustrate the manufacture of pharmaceutical preparations.

Example AA

Hard gelatine capsules can be produced as follows:

| Ingredients | mg/capsule |
|---|---|
| 1. Spray-dried powder containing 75% compound I | 20 |
| 2. Sodium dioctylsulphocuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120.0 |

The spray-dried powder, which is based on the active ingredient, gelatine and microcrystalline cellulose and which has an average active ingredient particle size of <1µ (measured by autocorrelation spectroscopy), is moistened with an aqueous solution of sodium carboxymethylcellulose and sodium dioctylsulphocuccinate and kneaded. The resulting mass is granulated. Dried and sieved, and the granulate obtained is mixed with microcrystalline cellulose, talc and magnesium stearate. The mixture is filled into size 0 capsules.

Example BB

| Ingredients | mg/tablet |
|---|---|
| 1. Compound I as a finely milled powder | 20 |
| 2. Powd. lactose | 100 |
| 3. whith corn starch | 60 |
| 4. Povidone K30 | 8 |
| 5. White corn starch | 112 |
| 6. Talc | 16 |
| 7. Magnesium stearate | 4 |
| Total | 320 |

Tablets can be produced as follows:

The finely milled substance is mixes with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

Example CC

Soft gelatine capsules can be produced as follows:

| Ingredients | mg/capsule |
|---|---|
| 1. Compound I | 5 |
| 2. Triglyceride | 450 |
| Total | 455 |

10 g of compound I are dissolved in 90 g of medium chain triglyceride with stirring, inert gasification and protection from light. This solution is processed as a capsule fill mass to soft gelatine capsules containing 5 mg of active ingredient.

Example DD

A dream can be produced from the ingredient listed hereinafter in a manner known per se:

| | Wt. % |
|---|---|
| Compound of Formula I | 0.1–5 |
| Cetyl alcohol | 5.25–8.85 |
| Arlacel 165 (glyceryl/PEG 100 stearate) | 3.75–6.25 |
| Miglyol 818 (caprylic/capric/linoleic acid) | 11.25–18.75 |
| Sorbitol solution | 3.75–6.25 |
| EDTA Na$_2$ | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

Example EE

A gel can be produced from the ingredients listed hereinafter in a manner known per se:

| | Wt. % |
|---|---|
| Compound of Formula I | 0.1–5 |
| Pluronic L101 (poloxamer 331) | 10.00 |
| Aerosil 200 (silicion dioxide) | 8.00 |
| PCL liquid (fatty acid ester) | 15.00 |
| Cetiol V (decyl oleate) | 20.00 |
| Neobee oil (medium chain length triglyceride) | 15.00 |
| Euhanol G (octyldodecanol), q.s. | 100.00 |

The physical properties of the preparations can be altered by varying the ratio between the adjuvants of Example 4

Example FF

A solution can be prepared from the following ingredients

| Ingredients | mg |
|---|---|
| Compound of formula I | 10 |
| Propylene glycol | 100 |
| Ethanol 94% (V/V) | 300 |
| Phosphoric acid ca. 85% | 5 |
| 1N NaOH ad pH 3 | |
| Demineralized water ad 1 ml | |

We claim:

1. A compound of the formula:

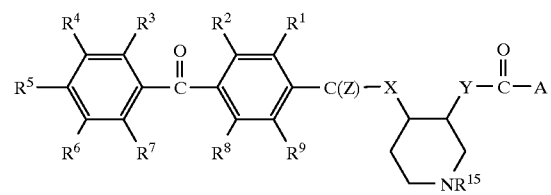

wherein

A is a residue

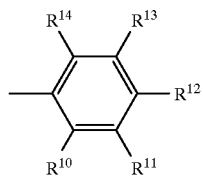

2-, 3- or 4-pyridyl or 2- or 3-piperazinyl, or 2-, 3- or 4-pyridyl or 2- or 3-piperazinyl substituted by one or more lower-alkyl, lower-alkoxy and hydroxy groups;

X and Y each independently are oxygen or NH, but are not both NH;

Z is oxygen or, where X is oxygen, oxygen or H,H;

$R^1$ is hydrogen;

$R^2$ is hydrogen or fluorine;

$R^3$ is hydrogen, hydroxy, lower-alkoxy, fluorine, trifluoromethyl, lower-alkoxycarbonyl, tetrazolyl or tetrazolyl substituted by lower-alkyl, benzyl, cyanomethyl or carbamoyl-methyl;

$R^4$ is hydrogen, hydroxy, lower-alkoxy, lower-alkyl, chlorine, fluorine, trifluoromethyl, acetyl, di-lower-akylamino, or lower-alkoxy-lower-alkyl, lower-alkylthio, lower-alkylsulphonyl, phenyl, pyrrolidinyl or piperidinyl;

$R^5$ is hydrogen, lower-alkoxy, fluorine or trifluoromethyl;

$R^6$ is hydrogen, hydroxy, lower-alkoxy, fluorine, 2,4-difluorophenyl, lower-alkoxy-lower-alkyl, lower-alkanoyl, benzoyl, nitrilo, trifluoromethyl, cyclo-lower-alkyl, 2- or 4-thiazolyl, 2-thiazolidinyl, 2-oxazolyl, 2-oxazolidinyl, or 2- or 4-imidazolyl;

$R^7$ is hydrogen, hydroxy, lower-alkoxy, amino or fluorine;

$R^6$ and $R^7$ together are a residue —N=CH—CH=N— or —N(CH$_3$)CH$_2$CH$_2$N(CH$_3$)—;

$R^8$ is hydrogen or fluorine;

$R^9$ is hydrogen;

$R^{10}$ is hydrogen, hydroxy, lower-alkoxy or lower-alkyl;

$R^{11}$ is hydrogen, lower-alkoxy, lower-alkyl, fluorine or bromine;

$R^{12}$ is hydrogen, hydroxy, lower-alkoxy, carboxy, lower-alkoxycarbonyl or amino;

$R^{13}$ is hydrogen, hydroxy, lower-alkoxy, lower-alkyl, acetyl or fluorine;

$R^{14}$ is hydrogen, lower-alkyl or fluorine;

$R^{15}$ is hydrogen or amidino;

$R^3$ and $R^4$ together are a residue —CH=CH—CH=CH— or ethylenedioxy;

$R^4$ and $R^5$ together are a residue —CH=CH—CH=CH—, tetra-methylene, methylenedioxy, ethylenedioxy or a residue —N=CH—CH=CH—; and $R^{12}$ and $R^{13}$ together are a residue —CH=CH—CH=CH— or —C(OH)=CH—CH=CH— in which the carbon atom carrying the hydroxy group is bonded at the $R^{12}$ position;

and pharmaceutically acceptable salts thereof.

2. The compound of claim 1 having the formula:

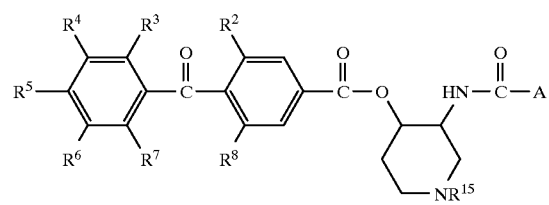

wherein $R^2$—$R^8$, $R^{15}$ and A are as in claim 1.

3. The compound of claim 2 wherein $R^2$ and $R^8$ are flourine.

* * * * *